(12) United States Patent
Baker et al.

(10) Patent No.: US 12,233,064 B1
(45) Date of Patent: Feb. 25, 2025

(54) **ANTARCTIC TUNICATE *SYNOICUM* SPECIES-DERIVED ALKALOIDS AND METHODS OF TREATMENT**

(71) Applicant: University of South Florida, Tampa, FL (US)

(72) Inventors: Bill J. Baker, Tampa, FL (US); Laurent J. Calcul, Tampa, FL (US); Kim Pham, Davie, FL (US); Sofia Kokkaliari, Tampa, FL (US); Alexander Dettmar Crawford, Oslo (NO); Nargess Shahbazi, Innsbruck (AT)

(73) Assignees: University of South Florida, Tampa, FL (US); Norwegian University of Life Sciences (NMBU), Oslo (NO)

( * ) Notice: Subject to any disclaimer, the term of this patent is extended or adjusted under 35 U.S.C. 154(b) by 228 days.

(21) Appl. No.: 16/926,003

(22) Filed: Jul. 10, 2020

Related U.S. Application Data

(60) Provisional application No. 62/873,607, filed on Jul. 12, 2019.

(51) Int. Cl.
| | |
|---|---|
| *A61K 31/506* | (2006.01) |
| *A61P 25/28* | (2006.01) |
| *A61P 33/06* | (2006.01) |
| *A61P 35/00* | (2006.01) |

(52) U.S. Cl.
CPC ............ *A61K 31/506* (2013.01); *A61P 25/28* (2018.01); *A61P 33/06* (2018.01); *A61P 35/00* (2018.01)

(58) Field of Classification Search
CPC ........ A61K 31/506; A61P 25/28; A61P 33/06; A61P 35/00

USPC .......................................................... 514/575
See application file for complete search history.

(56) References Cited

FOREIGN PATENT DOCUMENTS

WO    WO-2006075152 A1 *   7/2006   ............. A61P 11/00

OTHER PUBLICATIONS

Gompel M, (. Meridianins, a new family of protein kinase inhibitors isolated from the ascidian Aplidium meridianum. Bioorg Med Chem Lett. Apr. 5, 2004;14(7):1703-7. doi: 10.1016/j.bmcl.2004.01.050. PMID: 15026054).*

Xu et al., Statistical cluster analysis of pharmaceutical solvents, International Journal of Pharmaceutics, vol. 339, 175-188, Mar. 12, 2007 (Year: 2007).*

Marti-Mestres et al., Emulsions in Health Care Applications—An Overview, Journal of Dispersion Science and Technology, vol. 23, No. 1-3, 2002 (Year: 2002).*

Palanisamy, S. K. et al. Natural Products Diversity of Marine Ascidians (Tunicates; Ascidiacea) and Successful Drugs in Clinical Development. Natural Products and Bioprospecting 2017, 7 (1), 1-111.

(Continued)

*Primary Examiner* — Kortney L. Klinkel
*Assistant Examiner* — Padmaja S Rao
(74) *Attorney, Agent, or Firm* — Michele L. Lawson; Smith & Hopen, P.A.

(57) ABSTRACT

Pharmaceutical compositions containing one of five novel alkaloids isolated from a deep water Antarctic tunicate and methods of uses thereof are presented. The alkaloids belong to a family of compounds with known central nervous system (CNS) activity. The compounds display more oxidation than other members of the family, which may bestow additional bioactivity.

5 Claims, 31 Drawing Sheets

(56) References Cited

OTHER PUBLICATIONS

Schmidt, E. W. et al. Origin and Variation of Tunicate Secondary Metabolites. Journal of Natural Products 2012, 75 (2), 295-304.

Seldes, A. M. et al. Identification of Two Meridianins from the Crude Extract of the Tunicate Aplidium Meridianum by Tandem Mass Spectrometry. Natural Product Research 2007, 21 (6), 555-563.

Franco, L. H. et al. Indole Alkaloids from the Tunicate Aplidium m Eridianum. Journal of Natural Products 1998, 61 (9), 1130-1132.

Hahn, D. et al. A Novel Bromoindole Alkaloid from a Korean Colonial Tunicate *Didemnum* Sp. Natural Product Sciences 2015, 21 (4), 278-281.

Reyes, F. et al. Aplicyanins A-F, New Cytotoxic Bromoindole Derivatives from the Marine Tunicate Aplidium Cyaneum. Tetrahedron 2008, 64 (22), 5119-5123.

Diyabalanage, T. et al. Palmerolide A, a Cytotoxic Macrolide from the Antarctic Tunicate Synoicum a Dareanum. Journal of the American Chemical Society 2006, 128 (17), 5630-5631.

Noguez, J. H. et al. Palmerolide Macrolides from the Antarctic Tunicate Synoicum Adareanum. Bioorganic & Medicinal Chemistry 2011, 19 (22), 6608-6614.

Kingston, D. G., Modern natural products drug discovery and its relevance to biodiversity conservation. Journal of natural products 2010, 74 (3), 496-511.

Lebar, M. D., Antarctic tunicates and endophytic fungi: chemical investigation and synthesis / by Matthew D. Lebar. [Tampa, Fla.] : University of South Florida, 2010.

Seldes, A. et al. Identification of two meridianins from the crude extract of the tunicate Aplidium meridianum by tandem mass spectrometry. Natural product research 2007, 21 (6), 555-63.

Gompel, M. et al. Meridianins, a new family of protein kinase inhibitors isolated from the Ascidian Aplidium meridianum. Bioorganic & Medicinal Chemistry Letters 2004, 14 (7), 1703-1707.

Lebar, M. D. et al. CNS and antimalarial activity of synthetic meridianin and psammopemmin analogs. Bioorganic & medicinal chemistry 2011, 19 (19), 5756-62.

Walker, S. R. et al. Variolins and related alkaloids. Chemical reviews 2009, 109 (7), 3080-3098.

Volk, R. B. et al. Bromoanaindolone, a novel antimicrobial exometabolite from the cyanobacterium Anabaena constricta. Natural product research 2009, 23 (7), 607-612.

Lebar, M.D. et al. CNS and Antimalarial Activity of Synthetic Meridianin and Psammopemmin Analogs. Bioorganic & Medicinal Chemistry 2011, 19 (19), 5756-5762.

Lebar, M. D. and Baker, B. J. Synthesis and Structure Reassessment of Psammopemmin A. Australian Journal of Chemistry 2010, 63 (6), 862-866.

\* cited by examiner

Meridianin A: $R_1$=OH; $R_2$=$R_3$=$R_4$=H

Meridianin B: $R_1$=OH; $R_2$=$R_4$=H; $R_3$=Br

Meridianin C: $R_1$=$R_3$=$R_4$=H; $R_2$=Br

Meridianin D: $R_1$=$R_2$=$R_4$=H; $R_3$=Br

Meridianin E: $R_1$=OH; $R_2$=$R_3$=H, $R_4$=Br

Meridianin F: $R_2$=$R_3$=Br

Meridianin G: $R_1$=$R_2$=$R_3$=$R_4$=H

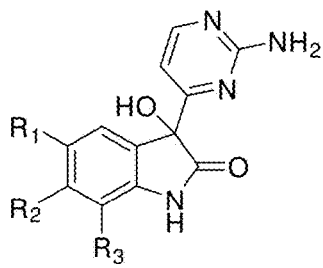
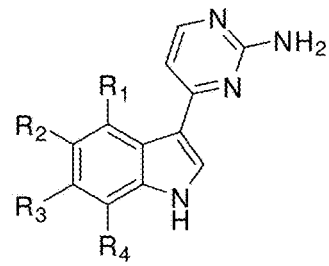

Australindolone A (1) $R_1=R_2=R_3=H$
Australindolone B (2) $R_1=Br\ R_2=R_3=H$
Australindolone C (3) $R_1=R_3=H\ R_2=Br$
Australindolone D (4) $R_1=R_2=Br\ R_3=H$ Meridianin A (5) $R_1=OH\ R_2=R_3=R_4=H$
Meridianin B (6) $R_1=OH\ R_2=R_4=H\ R_3=Br$
Meridianin C (7) $R_1=R_3=R_4=H\ R_2=Br$
Meridianin D (8) $R_1=R_2=R_4=H\ R_3=Br$
Meridianin E (9) $R_1=OH\ R_2=R_3=H\ R_4=Br$
Meridianin F (10) $R_1=R_4=H\ R_2=R_3=Br$
Meridianin G (11) $R_1=R_2=R_3=R_4=H$
Meridianin H (12) $R_1=OH\ R_2=R_4=Br\ R_3=H$

Figure 2

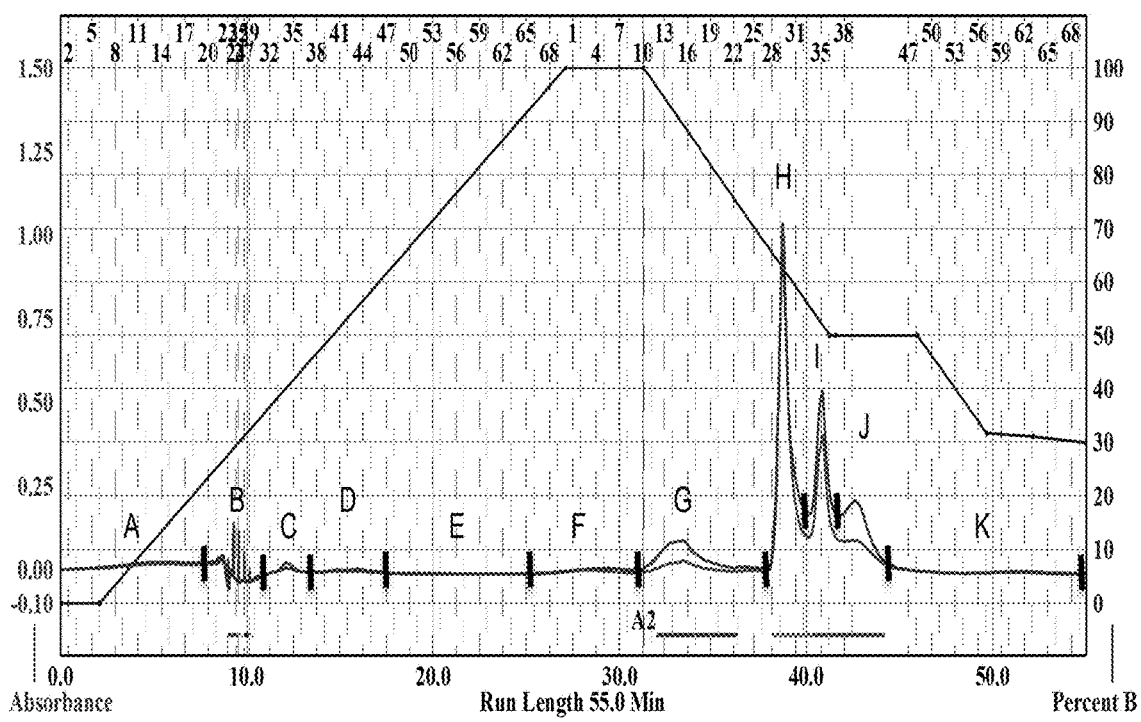

Figure 3

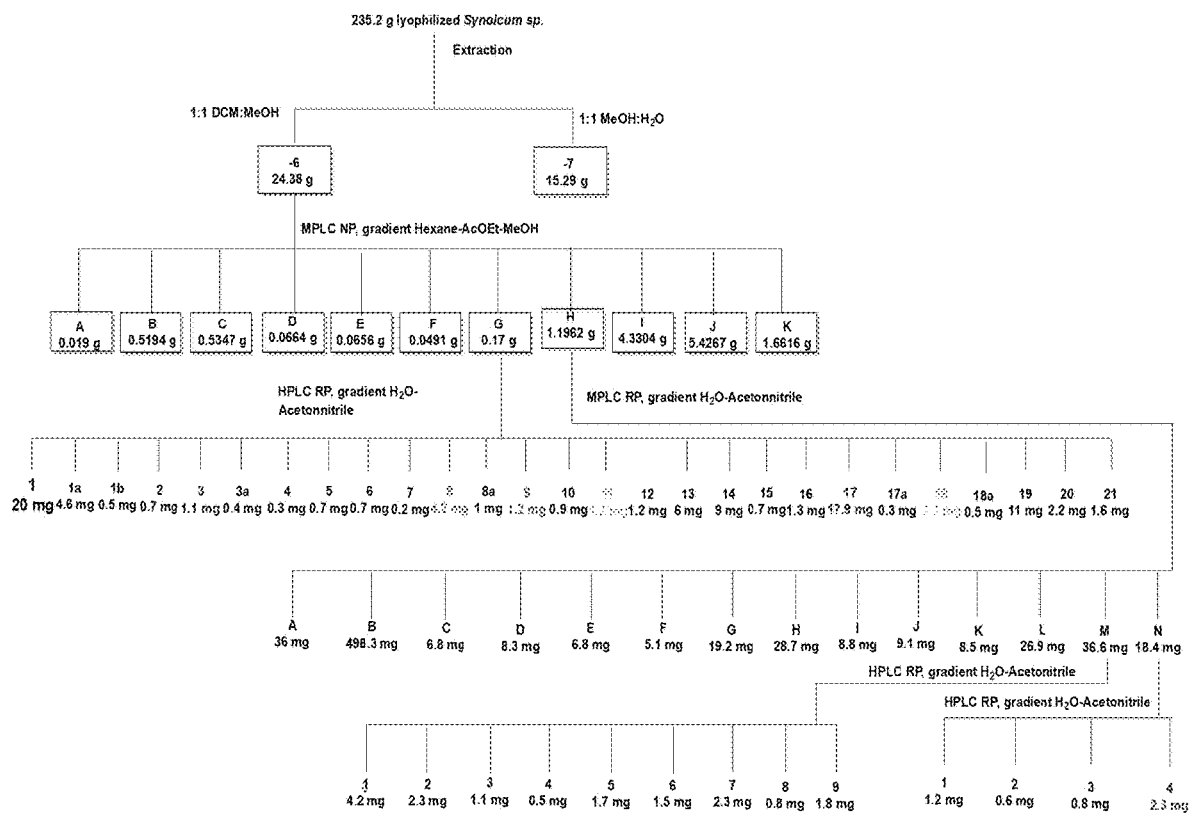
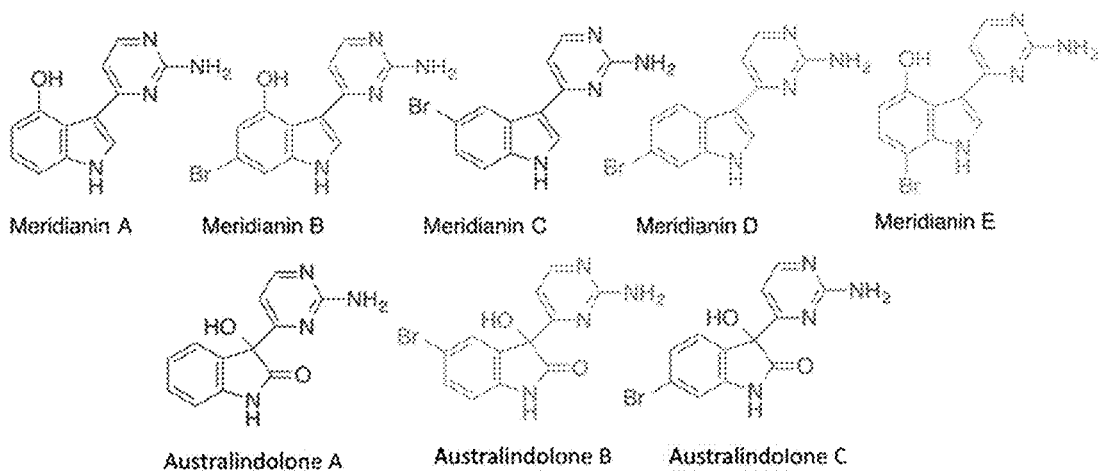
Figure 6

ANTARCTIC TUNICATE *SYNOICUM* SPECIES-DERIVED ALKALOIDS AND METHODS OF TREATMENT

CROSS REFERENCE TO RELATED APPLICATIONS

This application is a nonprovisional of and claims priority to U.S. Provisional Patent Application Ser. No. 62/873,607, entitled "Antarctic Tunicate *Synoicum* Species-Derived Alkaloids and Methods of Treatment", filed Jul. 12, 2019, the contents of which are hereby incorporated by reference into this disclosure.

FIELD OF INVENTION

This invention relates to novel alkaloids derived from *Synoicum* sp. and methods of use. More specifically, the present invention provides therapeutic methods and compositions for treating various disorders, using novel alkaloids derived from Antarctic invertebrates in the *Synoicum* sp.

BACKGROUND OF THE INVENTION

Marine invertebrates have been the source of a multitude of bioactive compounds in recent years, with interest drawn specially to sponges and tunicates. (Holland, L. Z. Tunicates. *Current Biology* 2016, 26 (4), R146-R152; Palanisamy, S. K.; Rajendran, N. M.; Marino, A. Natural Products Diversity of Marine Ascidians (Tunicates; Ascidiacea) and Successful Drugs in Clinical Development. Natural Products and Bioprospecting 2017, 7 (1), 1-111; Schmidt, E. W.; Donia, M. S.; McIntosh, J. A.; Fricke, W. F.; Ravel, J. Origin and Variation of Tunicate Secondary Metabolites. *Journal of Natural Products* 2012, 75 (2), 295-304). Tunicates can be found in both shallow and deep waters, and due to their extensive biodiversity can potentially be a great source for biodiscovery. (Carroll, A. R.; Copp, B. R.; Davis, R. A.; Keyzers, R. A.; Prinsep, M. R. Marine Natural Products. *Natural Product Reports* 2019, 36 (1), 122-173; Puglisi, M. P.; Sneed, J. M.; Ritson-Williams, R.; Young, R. Marine Chemical Ecology in Benthic Environments. *Natural Product Reports* 2019). Furthermore, only a small number of deep-water organisms have been analyzed due to the difficulties in accessing deep sea habitats. Most of the compounds isolated from tunicates are nitrogen-containing compounds, with the most common being aromatic alkaloids and macrocyclic metabolites. (Seldes, A. M.; Rodriguez Brasco, M. F.; Hernandez Franco, L.; Palermo, J. A. Identification of Two Meridianins from the Crude Extract of the Tunicate *Aplidium meridianum* by Tandem Mass *Spectrometry. Natural Product Research* 2007, 21 (6), 555-563; Franco, L. H.; Joffe, E. B. de K.; Puricelli, L.; Tatian, M.; Seldes, A. M.; Palermo, J. A. Indole Alkaloids from the Tunicate *Aplidium meridianum. Journal of Natural Products* 1998, 61 (9), 1130-1132; Hahn, D.; Kim, G. J.; Choi, H.; Kang, H. A Novel Bromoindole Alkaloid from a Korean Colonial Tunicate *Didemnum* Sp. Natural Product Sciences 2015, 21 (4), 278; Reyes, F.; Fernández, R.; Rodriguez, A.; Francesch, A.; Taboada, S.; Ávila, C.; Cuevas, C. Aplicyanins A-F, New Cytotoxic Bromoindole Derivatives from the Marine Tunicate *Aplidium cyaneum*. Tetrahedron 2008, 64 (22), 5119-5123; Diyabalanage, T.; Amsler, C. D.; McClintock, J. B.; Baker, B. J. Palmerolide A, a Cytotoxic Macrolide from the Antarctic Tunicate *Synoicum adareanum. Journal of the American Chemical Society* 2006, 128 (17), 5630-5631; Noguez, J. H.; Diyabalanage, T. K. K.; Miyata, Y.; Xie, X.-S.; Valeriote, F. A.; Amsler, C. D.; McClintock, J. B.; Baker, B. J. Palmerolide Macrolides from the Antarctic Tunicate *Synoicum adareanum. Bioorganic & Medicinal Chemistry* 2011, 19 (22), 6608-6614)

The tunicates are a phylum of ascidiaceans that possess a body surrounded by a tunic, formed of carbohydrates and proteins that provide a protective layer that varies from a tough, cartilaginous covering to thin, gelatinous covering. As the tunicate grows, the tunic can increase in size, thereby continuing to cover the tunicates body, which contains a buccal opening, a ciliated pharynx, a stomach, an atrial exit, along with a rudimentary nervous system and vascular system.

The tunic has a large amount of cellulose, along with live tissue that is supplied with blood. The tunics of some species fuse together to form a single structure protecting the animals. The majority of tunicates spend their juvenile life motile, where the animal resembles a tadpole, followed by attachment to a substrate and transformation into a sedentary adult life.

Natural product chemistry is an innovative field and has been responsible for isolating countless novel compounds. Many of these compounds, along with their derivatives, have accounted for more than half of FDA-approved drugs. (Kingston, D. G., Modern natural products drug discovery and its relevance to biodiversity conservation. *Journal of natural products* 2010, 74 (3), 496-511).

One of the natural sources the field depends on for crude material collection is the deep-sea of *Antarctica*. Due to the Antarctic Circumpolar Current (ACC) acting as a barrier between the two oceanic environments, an abundance amount of unique marine organisms is often found within the icy, nutrient-rich water. (Whitworth III, T., The Antarctic circumpolar current. *Oceanus* 1988, 31 (2), 53-58). Thus, these cold-water organisms have been collected and studied for their novel chemical entities.

The meridianins, isolated from the Antarctic tunicates *Aplidium meridianum*, *A. falklandicum*, as well as *Synoicum* sp., are low micromolar inhibitors of various cyclin-dependent kinases, glycogen synthase kinase-3, protein kinase A, and other protein kinases. (Lebar, M. D., *Antarctic tunicates and endophytic fungi: chemical investigation and synthesis*/by Matthew D. Lebar. [Tampa, Fla.]. University of South Florida, 2010; Franco, L. H.; Joffé, E. B. d. K.; Puricelli, L.; Tatian, M.; Seldes, A. M.; Palermo, J. A., Indole Alkaloids from the Tunicate *Aplidium meridianum. Journal of Natural Products* 1998, 61 (9), 1130-1132; Seldes, A. M.; Brasco, M. F.; Franco, L. H.; Palermo, J. A., Identification of two meridianins from the crude extract of the tunicate *Aplidium meridianum* by tandem mass spectrometry. *Natural product research* 2007, 21 (6), 555-63; Gompel, M.; Leost, M.; De Kier Joffe, E. B.; Puricelli, L.; Franco, L. H.; Palermo, J.; Meijer, L., Meridianins, a new family of protein kinase inhibitors isolated from the Ascidian *Aplidium meridianum. Bioorganic & Medicinal Chemistry Letters* 2004, 14 (7), 1703-1707; Lebar, M. D.; Hahn, K. N.; Mutka, T.; Maignan, P.; McClintock, J. B.; Amsler, C. D.; van Olphen, A.; Kyle, D. E.; Baker, B. J., CNS and antimalarial activity of synthetic meridianin and psammopemmin analogs. *Bioorganic & medicinal chemistry* 2011, 19 (19), 5756-62).

One of the organisms that were acquired during a collection trip to *Antarctica* is a yellow top tunicate *Synoicum* sp. Previous study on *Synoicum* sp. revealed a variety of meridianin derivatives (Meridianin A-C, E). (Lebar, M. D., *Antarctic tunicates and endophytic fungi: chemical investigation and synthesis*/by Matthew D. Lebar. [Tampa, Fla.]. University of South Florida, 2010). They are indole alkaloid derivatives that were first isolated from *Aplidium meridianum*, a tunicate from South Georgia Islands. (Franco, L. H.; Joffe, E. B. d. K.; Puricelli, L.; Tatian, M.; Seldes, A. M.; Palermo, J. A., Indole Alkaloids from the Tunicate *Aplidium meridianum*. *Journal of Natural Products* 1998, 61 (9), 1130-1132).

Meridianins consist of 2-aminopyrimidine substituted at C-3 of an indole skeleton that comes with or without bromine and/or hydroxyl group. Almost a decade later since the first isolation, another study revealed two other meridianin derivatives, which totaled to seven different types of Meridianin.

Meridianin A, which has been previously synthesized using a Bredereck protocol and through a one pot Masuda borylation-Suzuki coupling, was found to inhibit CDK1 (IC50=2.5 lM), CDK5 (3.5 lM), PKA (11.0 lM), PKG (200 lM), and GSK3-b (1.3 lM) while showing no toxic effects toward Hep2, HT29, and LMM3 cell lines (IC50>100 lM). (Walker, S. R.; Carter, E. J.; Huff, B. C.; Morris, J. C., Variolins and related alkaloids. *Chemical reviews* 2009, 109 (7), 3080-3098; Volk, R. B.; Girreser, U.; Al-Refai, M.; Laatsch, H., Bromoanaindolone, a novel antimicrobial exometabolite from the cyanobacterium *Anabaena constricta*. *Natural product research* 2009, 23 (7), 607-612; Gompel, M.; Leost, M.; De Kier Joffe, E. B.; Puricelli, L.; Franco, L. H.; Palermo, J.; Meijer, L., Meridianins, a new family of protein kinase inhibitors isolated from the Ascidian *Aplidium meridianum*. *Bioorganic & Medicinal Chemistry Letters* 2004, 14 (7), 1703-1707).

Additionally, meridianin A inhibited CDK2 (IC50=3.10 lM), CDK9 (2.40 lM), CK1 (1.10 lM) but was nontoxic toward SH-SY5Y cells (IC50>30 lM). Naturally occurring meridianins were found to deter predation against the common Antarctic omnivorous predator *Odontaster validus*. (Seldes, A. M.; Brasco, M. F.; Franco, L. H.; Palermo, J. A., Identification of two meridianins from the crude extract of the tunicate *Aplidium meridianum* by tandem mass spectrometry. *Natural product research* 2007, 21 (6), 555-63). A variety of synthetic routes to form meridianins and related bioactive analogs have been devised, and subsequently reviewed. (Walker, S. R.; Carter, E. J.; Huff, B. C.; Morris, J. C. Chem. Rev. 2009, 109, 3080).

The inventors were prompted to investigate the binding affinity of several of the 3-pyrimidylindoles to various serotonin receptors due to the structural features (amine-containing indolol) common to the compounds and serotonin (5-hydroxytryptamine, 5-HT). Serotonin transmission is thought to play a role in central nervous system (CNS) disorders. Compounds that bind to specific serotonin receptor subtypes can lead to treatment of CNS diseases. Selective antagonists of 5-HT2C helped to establish the receptor's role in behaviors such as feeding and anxiety. Neuropsychiatric disorders such as major depression as well as anxiety, and migraine are currently being treated with 5-HT selective receptor ligands while drugs that target the 5-HT2A receptor are under clinical investigation for the treatment of schizophrenia.

Pyrimidine containing compounds (e.g., pyrimethamine) have been used to combat malaria, a devastating disease affecting disadvantaged populations worldwide. Because many current treatments for malaria are losing efficacy due to drug-resistant parasites, new drugs are required to overcome resistance. Meridianin analogs substituted with both 20-piperidinyl and 60-aryl moieties have been reported to display a minimum inhibitory concentration of 1-10 lg/mL (MIC=_3-30 lM) versus the malaria parasite *Plasmodium falciparum* NF-54. The inventors investigated whether the 3-pyrimidylindole compounds could also inhibit the malaria parasite.

In the continuing search for new bioactive compounds, an extract of a *Synoicum* sp. tunicate collected in Antarctica was screened in a developmental zebrafish assay. The extract demonstrated an interesting phenotype in the assay and therefore led to further investigation. In previous reports, Meridianins A-G, which belong in the indole alkaloid family, were isolated from *Synoicum* sp and *Aplidium meridianum*. (Kyle, D. E.; Baker, B. J. CNS and Antimalarial Activity of Synthetic Meridianin and Psammopemmin Analogs. *Bioorganic & Medicinal Chemistry* 2011, 19 (19), 5756-5762; Lebar, M. D.; Baker, B. J. Synthesis and Structure Reassessment of Psammopemmin A. *Australian Journal of Chemistry* 2010, 63 (6), 862).

Once isolated, Meridianin A-G were tested for potential inhibiting activity against several protein kinases. Cyclin-dependent kinases (CDKs), Glycogen synthase kinase-3 (GSK-3), protein kinase A (PKA), and casein kinase 1 (CK1) assays were implemented, and all but Meridianin G show promising results. (Gompel, M.; Leost, M.; De Kier Joffe, E. B.; Puricelli, L.; Franco, L. H.; Palermo, J.; Meijer, L., Meridianins, a new family of protein kinase inhibitors isolated from the Ascidian *Aplidium meridianum*. *Bioorganic & Medicinal Chemistry Letters* 2004, 14 (7), 1703-1707). Synthetic Meridianin A, in particular, was also tested against *Plasmodium falciparum*, a parasite responsible for malaria epidemic. Meridianin A, in return, was found to inhibit the growth of *P. falciparum* but is also cytotoxic to A549 (Human lung adenocarcinoma epithelial cell line). (Lebar, M. D.; Hahn, K. N.; Mutka, T.; Maignan, P.; McClintock, J. B.; Amsler, C. D.; van Olphen, A.; Kyle, D. E.; Baker, B. J., CNS and antimalarial activity of synthetic meridianin and psammopemmin analogs. *Bioorganic & medicinal chemistry* 2011, 19 (19), 5756-62). Many Meridianin analogues were also synthesized and tested for their corresponding activities. (Walker, S. R.; Carter, E. J.; Huff, B. C.; Morris, J. C., Variolins and related alkaloids. *Chemical reviews* 2009, 109 (7), 3080-3098).

Given the complexity and pathways involved in kinase disorderss such as cancers and CNS disorders, what is needed are novel compositions and methods for treating such cancers, CNS disorders and parasitic infections.

SUMMARY OF THE INVENTION

The inventors have isolated four new indolone alkaloids, australindolones A-D (1-4), as well as a new indole alkaloid, meridianin H (12). The inventors also successfully isolated the previously reported meridianins A-G (5-11) to test their bioactivity. The isolation was guided using 1D proton NMR and a developmental zebrafish bioassay. All 8 meridianins showed bioactivity, exhibited as dysmorphology in the zebrafish embryos at various concentrations.

In an embodiment, a pharmaceutical composition comprising a synthetic compound of formula I is presented where Formula I comprises:

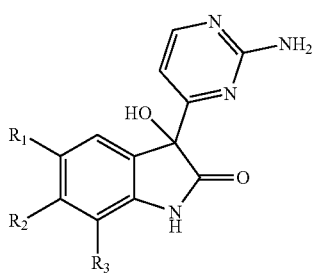

(I)

wherein R¹ is hydrogen or bromine;
wherein R² is hydrogen or bromine; and
wherein R³ is hydrogen.

The composition may further comprise a pharmaceutically acceptable carrier. In some embodiments of the composition, both R¹ and R² are hydrogen. In some embodiments of the composition, R¹ is hydrogen and R² is bromine. In some embodiments of the composition, R¹ is bromine and R² is hydrogen. In some embodiments of the composition, both R¹ and R² are bromine.

In an embodiment a pharmaceutical composition comprising a synthetic compound of Formula II is presented where Formula II comprises:

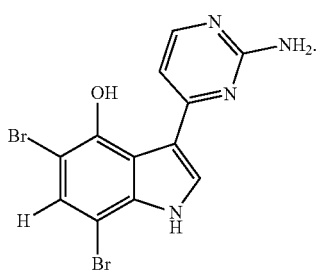

(II)

The composition may further comprise a pharmaceutically acceptable carrier.

In an embodiment, a method of treating a kinase disorder or parasitic infection in a patient in need thereof is presented comprising:
administering to the patient in need thereof a therapeutically effective amount of a pharmaceutical composition comprising the compound of Formula I or Formula II:

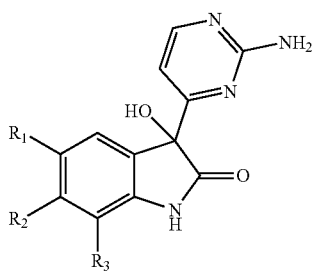

(I)

wherein R¹ is hydrogen or bromine;
wherein R² is hydrogen or bromine; and
wherein R³ is hydrogen; or

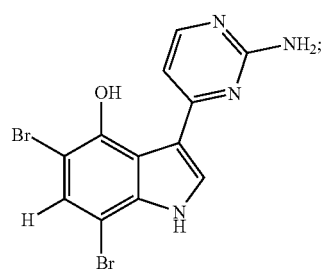

(II)

and
a pharmaceutically acceptable carrier.

In some embodiments of the composition, both R¹ and R² are hydrogen. In some embodiments of the composition, R¹ is hydrogen and R² is bromine. In some embodiments of the composition, R¹ is bromine and R² is hydrogen. In some embodiments of the composition, both R¹ and R² are bromine.

In some embodiments, the kinase disorder may be caused by altered signaling of cyclin-dependent kinases (CDKs), glycogen synthase kinase-3 (GSK-3), protein kinase A (PKA), casein kinase 1 (CK1), bone morphogenic protein (BMP), Janus kinase (JAK), mitogen-activated protein kinase (MAP) or combinations thereof.

In some embodiments, the kinase disorder may be selected from the group consisting of cancer, central nervous system (CNS) disorders, neurodegenerative diseases, mood disorders, inflammation, rheumatoid arthritis, and Crohn's disease.

The kinase disorder may be cancer selected from the group consisting of adenocarcinomas, lung cancers, gliomas, oligodendrogliomas, glioblastomas, astrocytomas, anaplastic oligodendroglioma, neuroblastomas, neuroepitheliomas, meningiomas, and nerve sheath tumors. In some embodiments, the cancer is lung cancer.

The parasitic infection may be malaria or Leishmaniasis. In some embodiments in which the parasitic infection is malaria, the malaria is caused by *Plasmodium falciparum*.

BRIEF DESCRIPTION OF THE DRAWINGS

For a fuller understanding of the invention, reference should be made to the following detailed description, taken in connection with the accompanying drawings, in which:

FIG. 2 is an image depicting Australindolones A-D and Meridianins A-H. New compounds are shown in bold.

FIG. 3 is a graph showing MPLC collection scheme of fraction NBP13-9.

FIG. 6 is an illustration showing fractionation scheme of NBP13-9. Highlighted fractions correspond to pure compounds.

DETAILED DESCRIPTION OF THE PREFERRED EMBODIMENT

Figure 1:
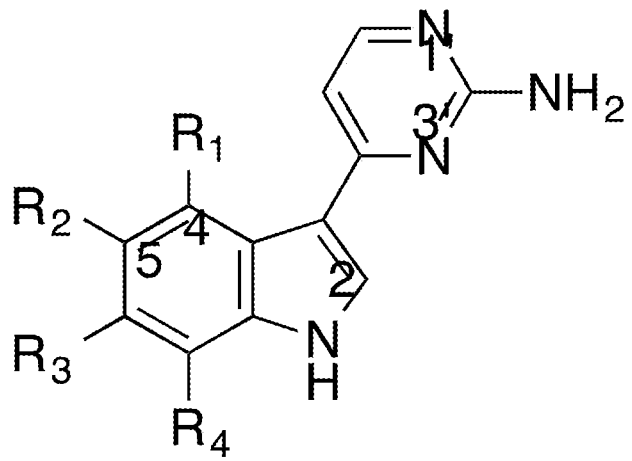
FIG. 1 illustrates the structure of known Meridianin A-G.
Figure 4:
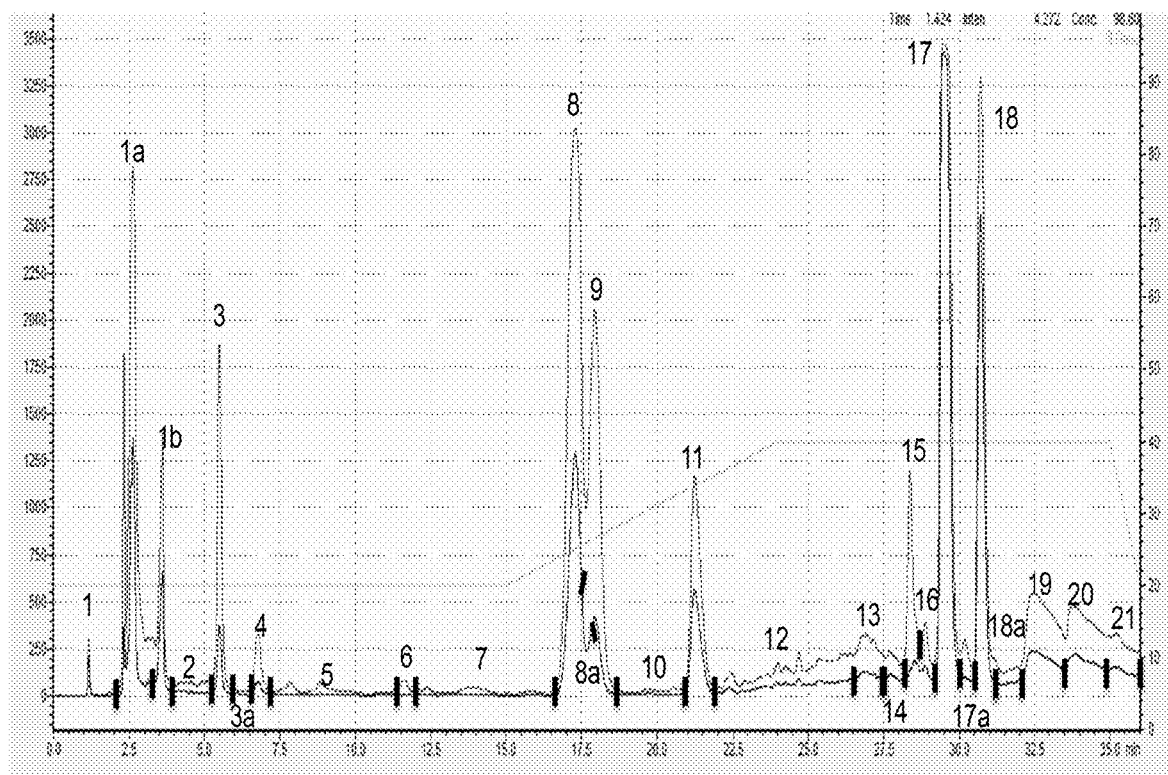
FIG. 4 is graph showing HPLC chromatogram collection scheme of fraction NBP13-9G.

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

All numerical designations, such as temperature, time, and concentration, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein Numerical data may be expressed or presented herein in a range format. Where a range of values is provided, it is understood that each intervening value, to the tenth of the unit of the lower limit, unless the context clearly dictates otherwise, between the upper and lower limits of that range is also specifically disclosed. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used herein, the singular forms "a," "an" and "the" include plural referents unless the context clearly dictates otherwise.

As used herein, "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. As used herein the term "about" refers to 1 15% of the numerical.

As used herein, the term "comprising" is intended to mean that the products, compositions, and methods include the referenced components or steps, but not excluding others. "Consisting essentially of" when used to define products, compositions, and methods, shall mean excluding other components or steps of any essential significance. "Consisting of" shall mean excluding more than trace elements of other components or steps.

"Patient" is used to describe an animal, preferably a human, to whom treatment is administered, including prophylactic treatment with the compositions of the present invention.

The "therapeutically effective amount" for purposes herein is thus determined by such considerations as are known in the art. A therapeutically effective amount of the pharmaceutical compositions and compounds described herein is that amount necessary to provide a therapeutically effective result in vivo. The amount of the compounds or pharmaceutical compositions must be effective to achieve a response, including but not limited to, total prevention of (e.g., protection against) and to improved survival rate or more rapid recovery, or improvement or elimination of symptoms associated with kinase disorders, neurological disorders, cancers, malaria, Leishmaniasis or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

"Administration" or "administering" is used to describe the process in which the compounds or pharmaceutical compositions of the present invention are delivered to a patient. The composition may be administered in various ways including parenteral (referring to intravenous and intraarterial and other appropriate parenteral routes), intrathecal, intraventricular, intracisternal, intranigral, oral, rectal, nasal, percutaneous, among others. The pharmaceutical compositions and compounds described herein may be administered independently or in combination with other compounds to treat a given disease. For example, in cancer treatment the pharmaceutical compositions and compounds may be administered with a chemotherapeutic agent.

The amount of the compound in the pharmaceutical composition will depend on absorption, distribution, metabolism, and excretion rates of the drug as well as other factors known to those of skill in the art. Dosage values may also vary with the severity of the condition to be alleviated. The compounds may be administered once or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. It is contemplated that one of ordinary skill in the art can determine and administer the appropriate dosage of compounds disclosed in the current invention according to the foregoing considerations.

Dosing frequency for the composition includes, but is not limited to, at least about once per day, at least once every other day, at least 3 times per week, at least twice per week, and at least once per week. In some embodiments, the interval between each administration is less than about 24 hours, such as less than about any of 23, 22, 21, 20, 19, 18, 17, 16, 15, 14, 13, 12, 11, 10, 9, 8, 7, 6, 5, 4, 3, 2, or 1 hour. In some embodiments, the interval between each administration is constant. For example, the administration can be carried out every hour, every two hours, every three hours, every four hours, every 5 hours, every six hours, every seven hours, every eight hours, every nine hours, every ten hours, every eleven hours, or every twelve hours. In some embodiments, the administration can be carried out twice daily, three times daily, or more frequent.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compounds used in the present invention may be administered individually, or in combination with or concurrently with one or more other compounds. Additionally, compounds used in the present invention may be administered in combination with or concurrently with other therapeutics for the particular disorders.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, 19$^{th}$ ed.) describes formulations which can be used in connection with the subject invention.

For ease of administration, the subject compounds may be formulated into various pharmaceutical forms. As appropriate compositions there may be cited all compositions usually employed for systemically or topically administering drugs. To prepare the pharmaceutical compositions of this invention, a naturally or synthetically formed Australindolone or Meridianin, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions.

"Treatment" or "treating" as used herein refers to any of the alleviation, amelioration, elimination and/or stabilization of a symptom, as well as delay in progression of a symptom of a particular disorder.

"Kinase disorder" as used herein refers to a disorder exhibiting altered kinase signaling of at least one kinase as compared to a normal control, particularly of cyclin-dependent kinases (CDKs), glycogen synthase kinase-3 (GSK-3), protein kinase A (PKA), casein kinase 1 (CK1), bone morphogenic protein (BMP), Janus kinase (JAK), mitogen-activated protein kinase (MAP) or combinations thereof. The compounds and pharmaceutical compositions described herein are useful as kinase inhibitors that can be used to treat kinase disorders. Examples of kinase disorders include, but are not limited to, cancers; central nervous system (CNS) disorders; neurodegenerative diseases including tau-related neuropathies; mood disorders; inflammation; rheumatoid arthritis; and Crohn's disease.

The term "cancer", "tumor", "cancerous", and malignant" as used herein, refer to the physiological condition in mammals that is typically characterized by unregulated cell growth. Examples of cancer include, but are not limited to, adenocarcinomas including, but not limited to, those of the lung, breast, colon, pancreas, and prostate; lung cancers including both small cell lung cancer and non-small cell lung cancer; tumors in neural tissue such as gliomas, oligodendrogliomas, glioblastomas, astrocytomas, anaplastic oligodendroglioma, neuroblastomas, neuroepitheliomas, meningiomas, and nerve sheath tumors.

The term "neurodegenerative disease" refers to any abnormal physical or mental behavior or experience where the death or dysfunction of neuronal cells is involved in the etiology of the disorder. Examples of neurodegenerative diseases include, but are not limited to, Alzheimer's disease, Parkinson's disease, Huntington's disease, dementia, amyotrophic lateral sclerosis (ALS), and multiple sclerosis.

"Parasitic infection" or "parasitic disease" as used herein refers to diseases caused by a parasite such as a protozoan. Examples of parasitic infections treated by the disclosed compounds and pharmaceutical compositions include, but are not limited to, malaria and Leishmaniasis.

The term "synthetic" or "synthetically derived" as used herein refers to a product produced artificially by human hand by chemical synthesis. In particular, "synthetic" refers to the manufacture of a product which mimics a natural product. Both natural and synthetic products can be used to manufacture the pharmaceutical compositions described herein.

The inventors have isolated five new compounds from yellow top tunicate *Synoicum* sp. and elucidated their structures for synthetic manufacture. The compounds can be synthetically created and combined with a pharmaceutically acceptable carrier to administered to a patient for use as kinase inhibitors that can treat a wide variety of diseases from cancers to neurodegenerative diseases such as Alzheimer's disease. The pharmaceutical compositions and compounds are also efficacious in treating diseases such as malaria and Leishmaniasis.

The following non-limiting examples illustrate the structures of the novel compounds as well as potential methods of use.

Example 1—General Procedures for Isolation of Meridianins

The yellow top tunicate *Synoicum* sp. was collected in the neighboring benthic zone of Palmer Station in *Antarctica*. The sample was then labeled as NBP13-9, and stored at −80° C. As a preliminary step, the sample was broken up into smaller pieces and lyophilized. 235.2 grams of the lyophilized sample was subjected to both polar and nonpolar solvents. The extract from the nonpolar solvent was dried and prepared as solid deposit by dissolving in methylene chloride and silica under vacuum. The solid deposit was then loaded into a cartridge for further extraction using medium pressure liquid chromatography (MPLC) method on a Teledyne Isco Combi-Flash Rf Instrument. The run started off with 100% of ethyl acetate then gradually exchanged for 100% of hexane over 27.1 minutes. Hexane continued to run through the column for 4.2 minutes, and then decreased to 29.8% by the replacement of methanol in a 3-steps binary gradient that took 23.7 minutes, seen in FIG. 3.

The run amassed a total of 55 minutes and ten fractions. Nuclear Magnetic Resonance (NMR) data was obtained for all fractions by using a Varian 500 Mhz cold-probe-equipped spectrometer, which guided to the extrapolation of fraction G and H due to their interesting peaks that correlate to those of indole alkaloids. Using a Shimadzu High Pressure Liquid Chromatography (HPLC) instrument and a Phenomenex Luna 5 m C18(2) reversed-phase semi-preparative column, a method was set up to further separate Fraction G into 26 sub-fractions. The optimized method consisted of an isocratic step at 20:80 acetonitrile (ACN):water over 15 minutes, an elevation step to 40:60 ACN:water in 9 minutes, and a final isocratic step at 40:60 ACN:water for 11 minutes, seen in FIG. 3.

Figure 7:
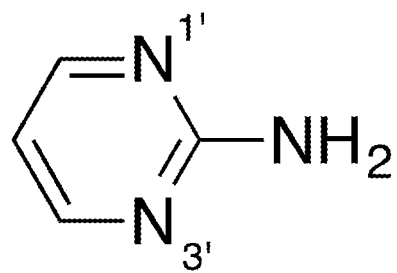
FIG. 7 is an illustration showing the 3-aminopyrimidine backbone.
Figure 8:
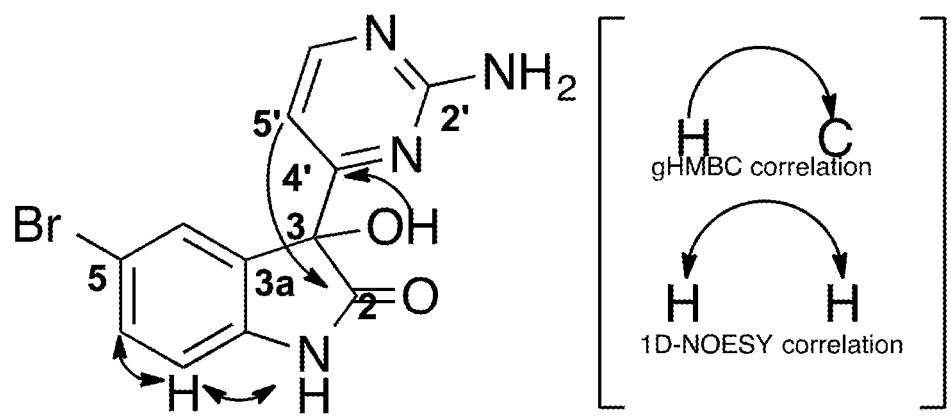
FIG. 8 is an illustration of the structure of isolated compound from fraction NBP13-9G-8 with gHMBC and 1D-NOESY correlations.

Identities of Meridianin A from sub-fraction 11 and Meridianin B from sub-fraction 18 were confirmed by comparing ESIMS and $^1$H NMR data with literature values, seen in Table 1, 2. Purified Meridianin E, from sub-fraction 17, was confirmed through $^1$H and $^{13}$C spectral data obtained from Varian 500 Mhz cold-probe-equipped spectrometer, and High Resolution Electrospray Ionization Mass Spectrometry (HRESIMS), seen in FIGS. 7 and 8.

Figure 11A:
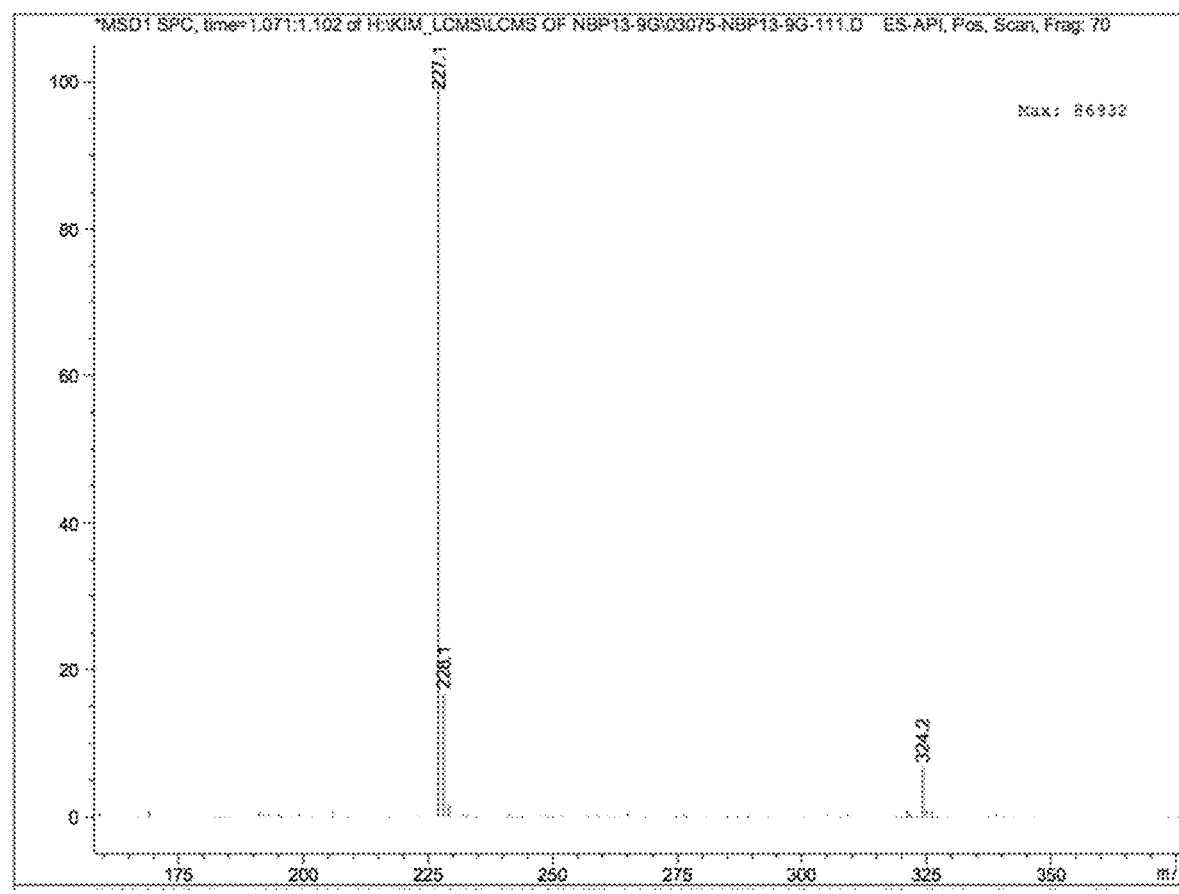
FIG. 11A is a graph of the ESIMS of Meridianin A from fraction NBP13-9G-11.
Figure 11B:
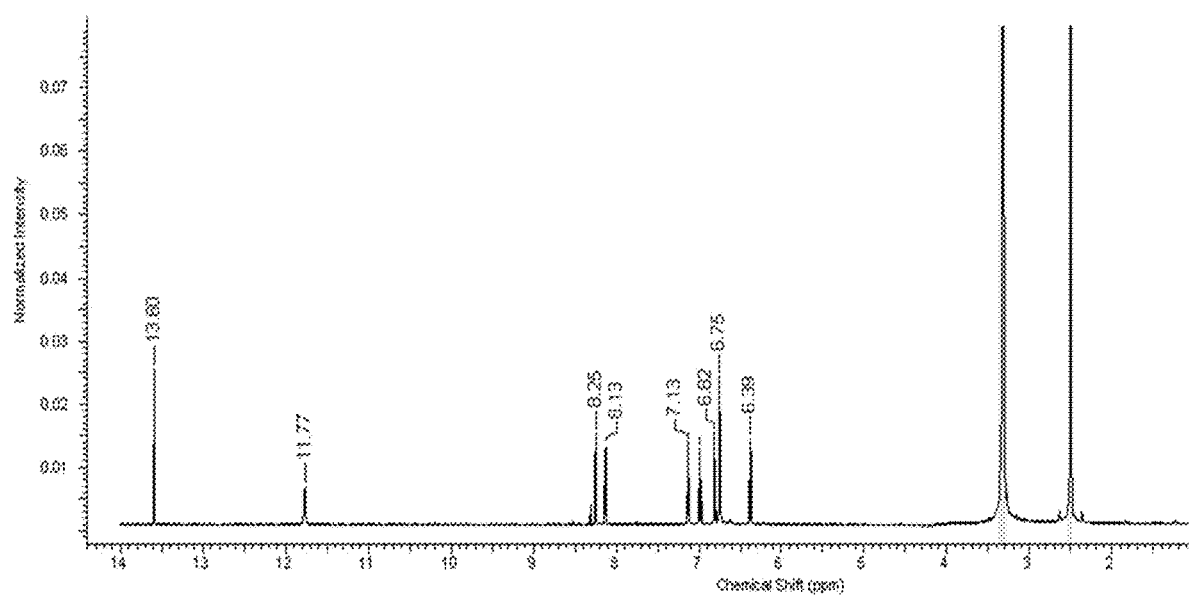
FIG. 11B is a graph of the NMR spectra (500 MHz, DMSO-$d_6$) of Meridianin A from fraction NBP13-9G-11.
Figure 11C:
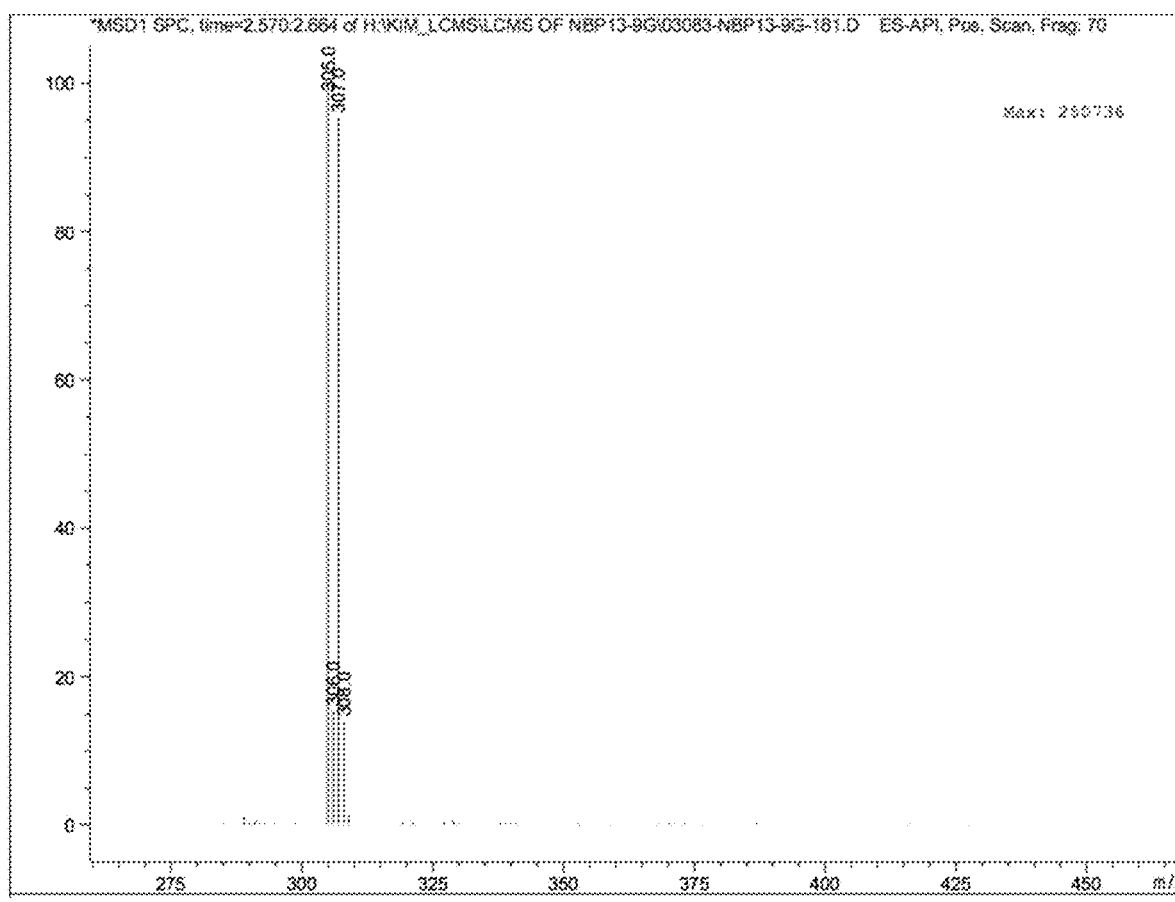
FIG. 11C is a graph of the ESIMS of Meridianin B from fraction NBP13-9G-18.
Figure 11D:
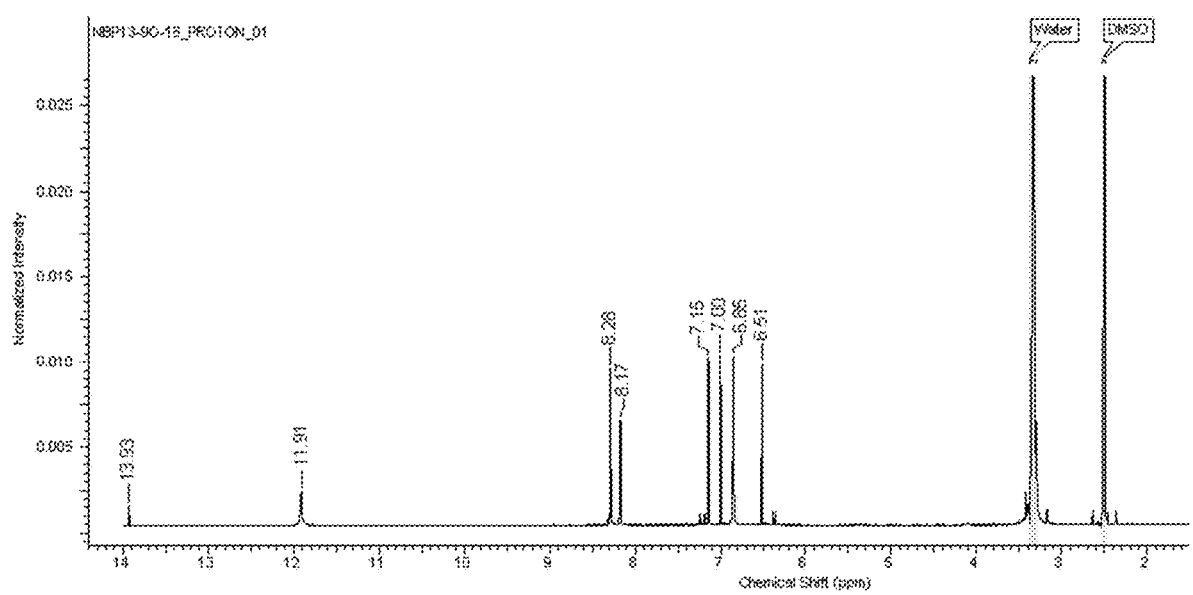
FIG. 11D is a graph of the $^1$H NMR spectra (500 MHz, DMSO-$d_6$) of Meridianin B from fraction NBP13-9G-18.
Figure 11E:
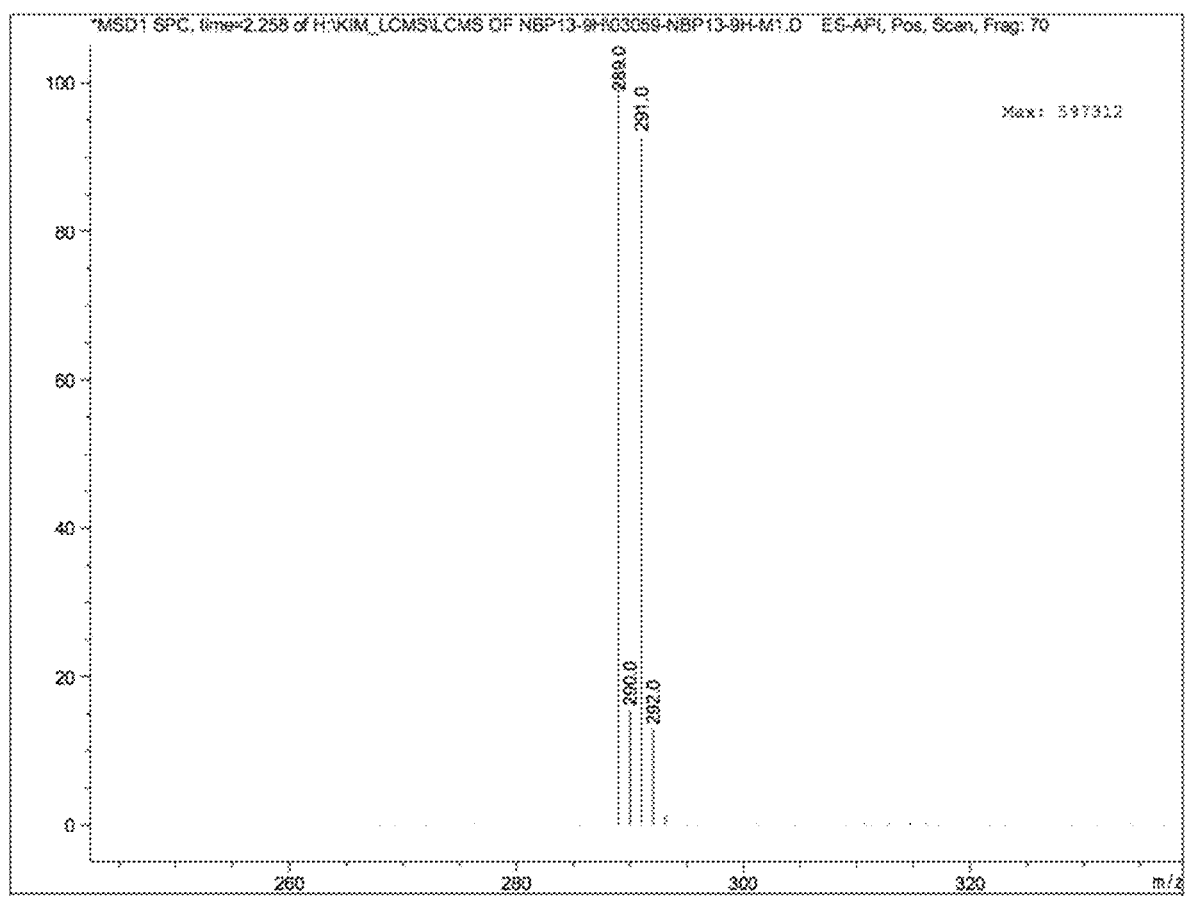
FIG. 11E is a graph of the ESIMS of Meridianin C from fraction NBP13-9H-M-3.
Figure 11F:
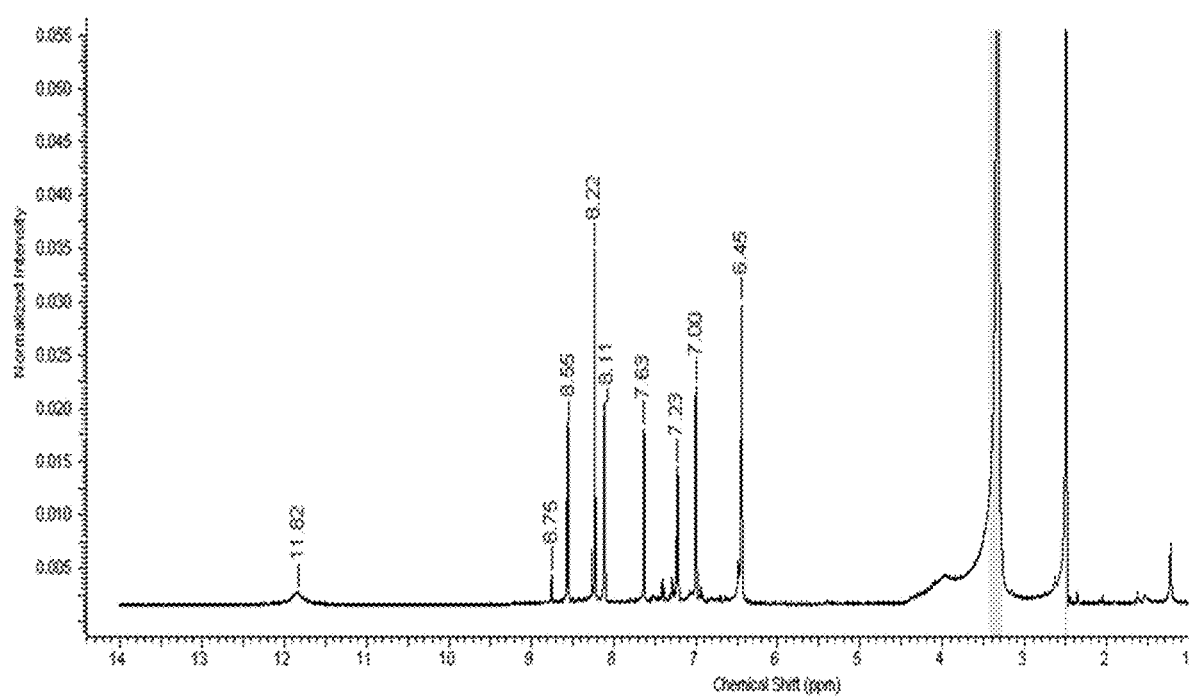
FIG. 11F is a graph of the NMR spectra (500 MHz, DMSO-$d_6$) of Meridianin C from fraction NBP13-9H-M-3.
Figure 11G:
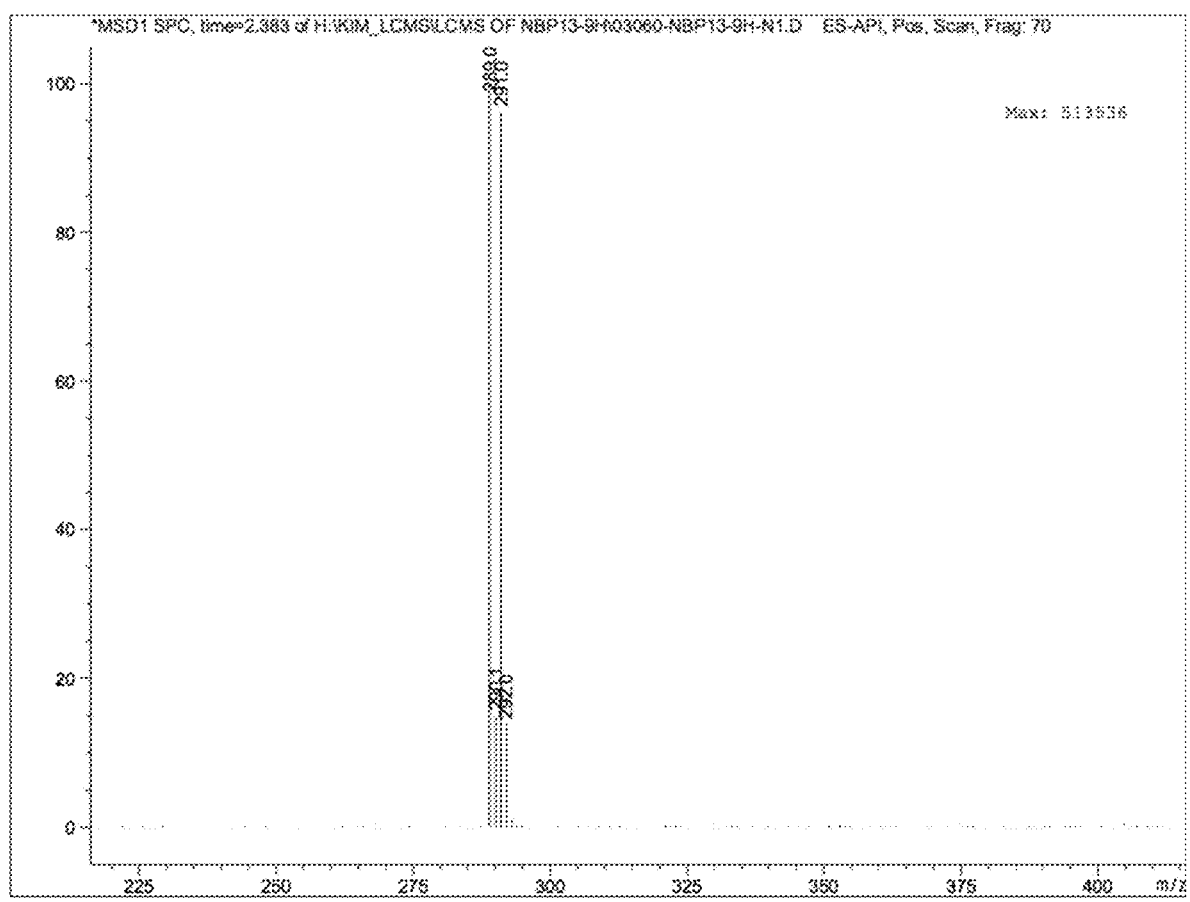
FIG. 11G is a graph of the ESIMS of Meridianin C from fraction NBP13-9H-N-4.
Figure 11H:
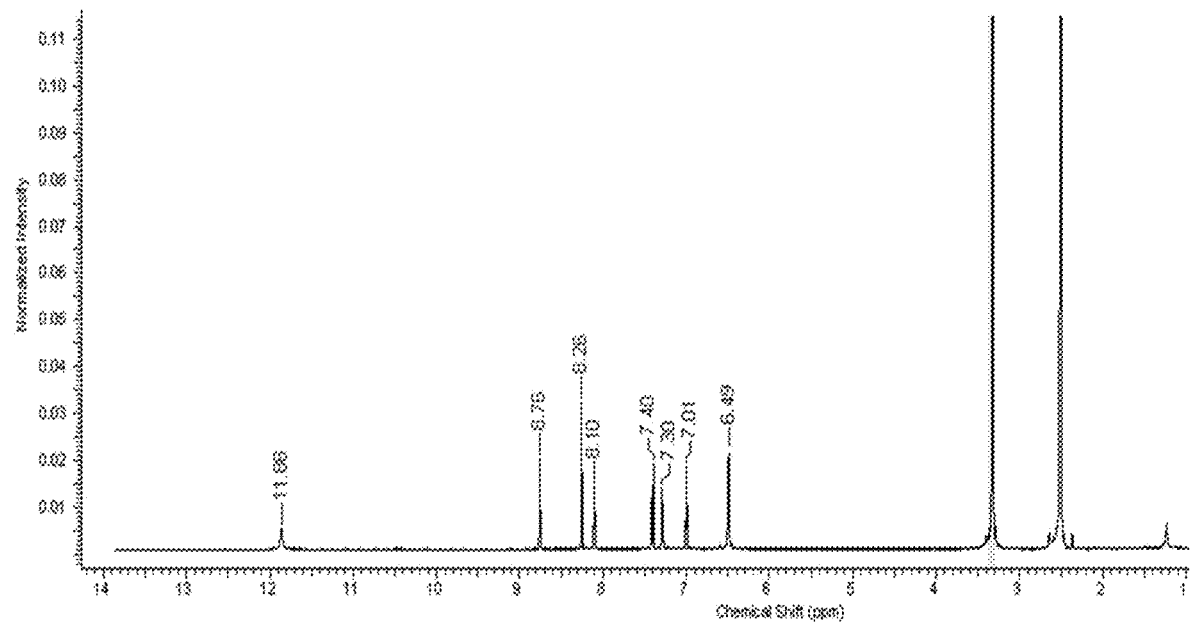
FIG. 11H is a graph of the $^1$H NMR spectra (500 MHz, DMSO-$d_6$) of Meridianin D from fraction NBP13-9H-N-4.
Figure 11I:
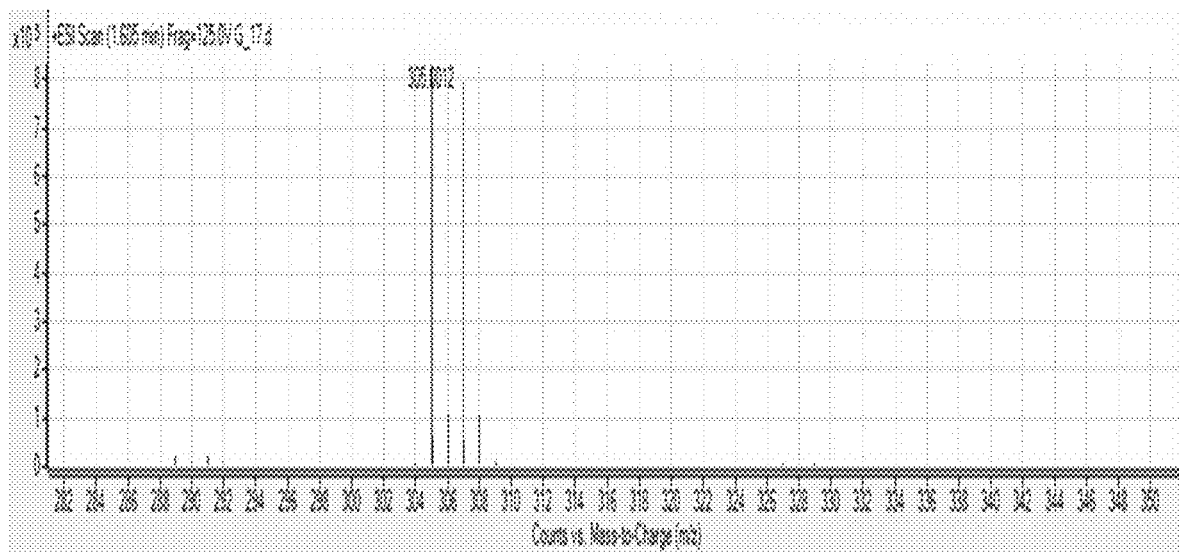
FIG. 11I is a graph of the resolution Mass Spectrometry (HRMS) data of purified Meridianin E from fraction NBP13-9G-17. HRMS=305.0012 m/z.
Figure 11J:
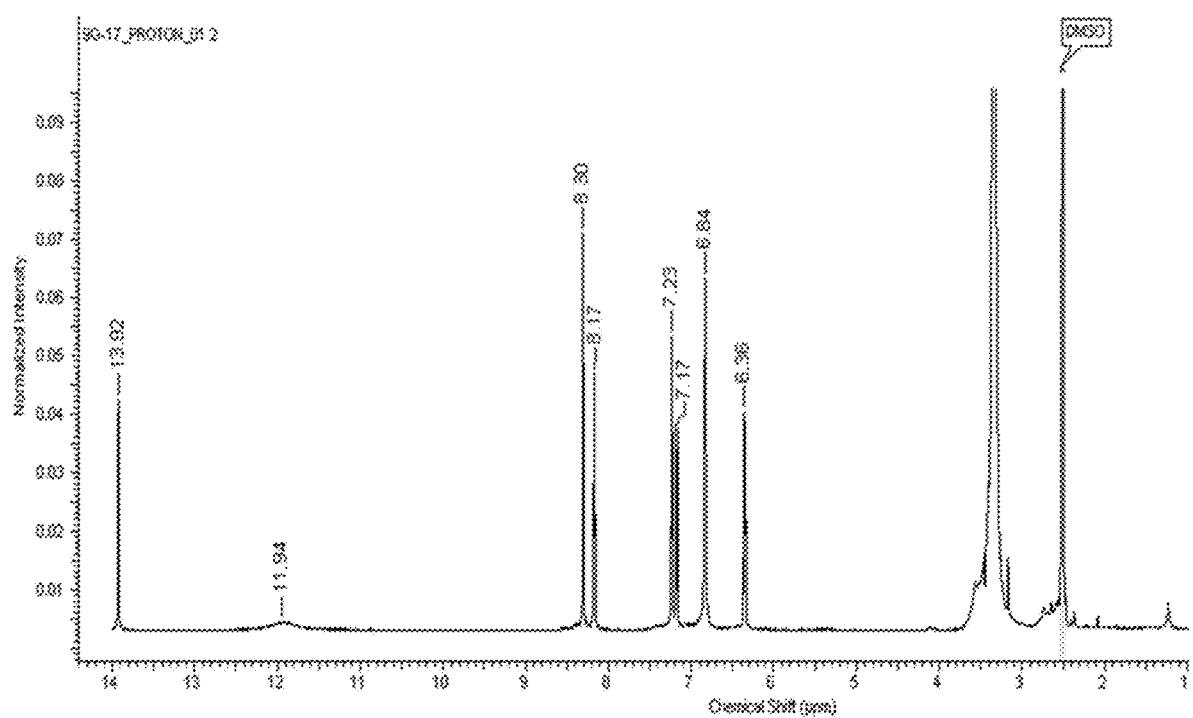
FIG. 11J is a graph showing NMR spectra (500 MHz, DMSO-$d_6$) of Meridianin E from fraction NBP13-9G-17.
Figure 11K:
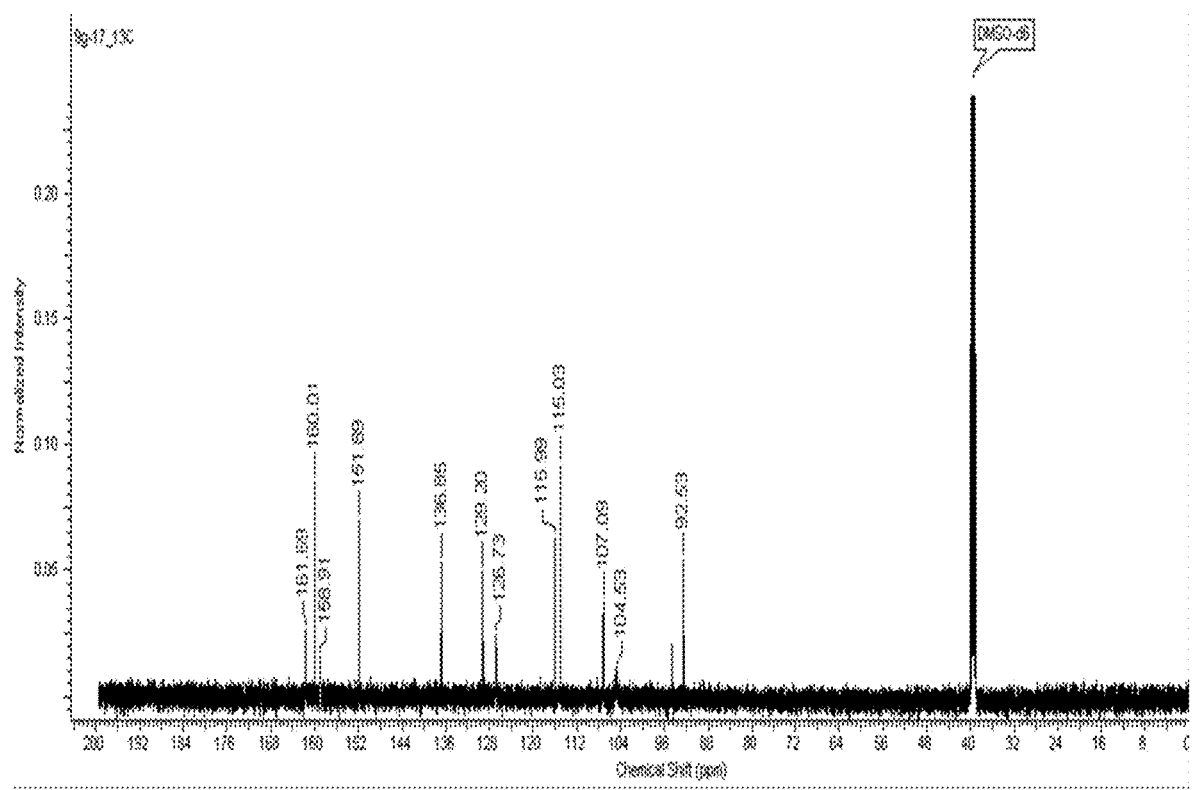
FIG. 11K is a graph showing $^{13}$C NMR spectra (500 MHz, DMSO-$d_6$) of Meridianin E from fraction NBP13-9G-17.
Figure 11L:
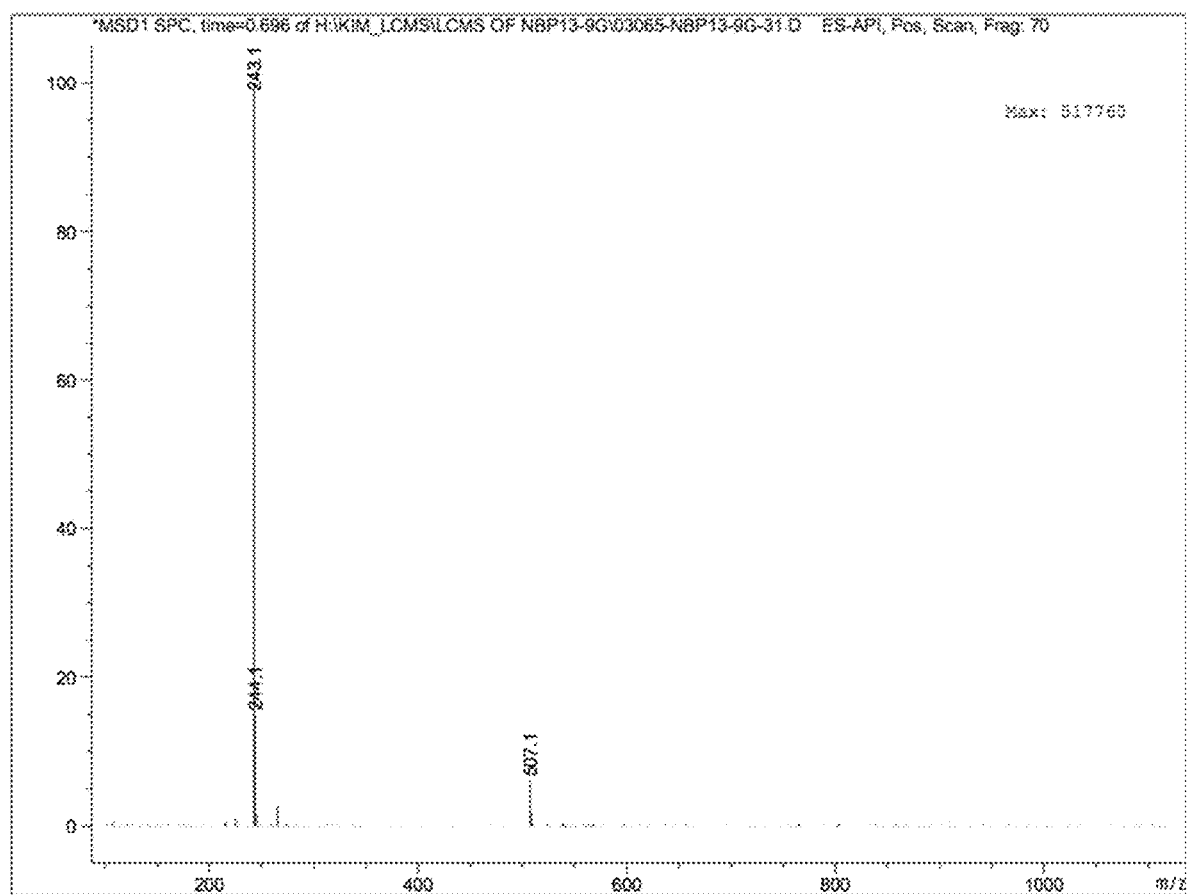
FIG. 11L is a graph showing ESIMS of Australindolone A (1) from fraction NBP13-9G-3.
Figure 11M:
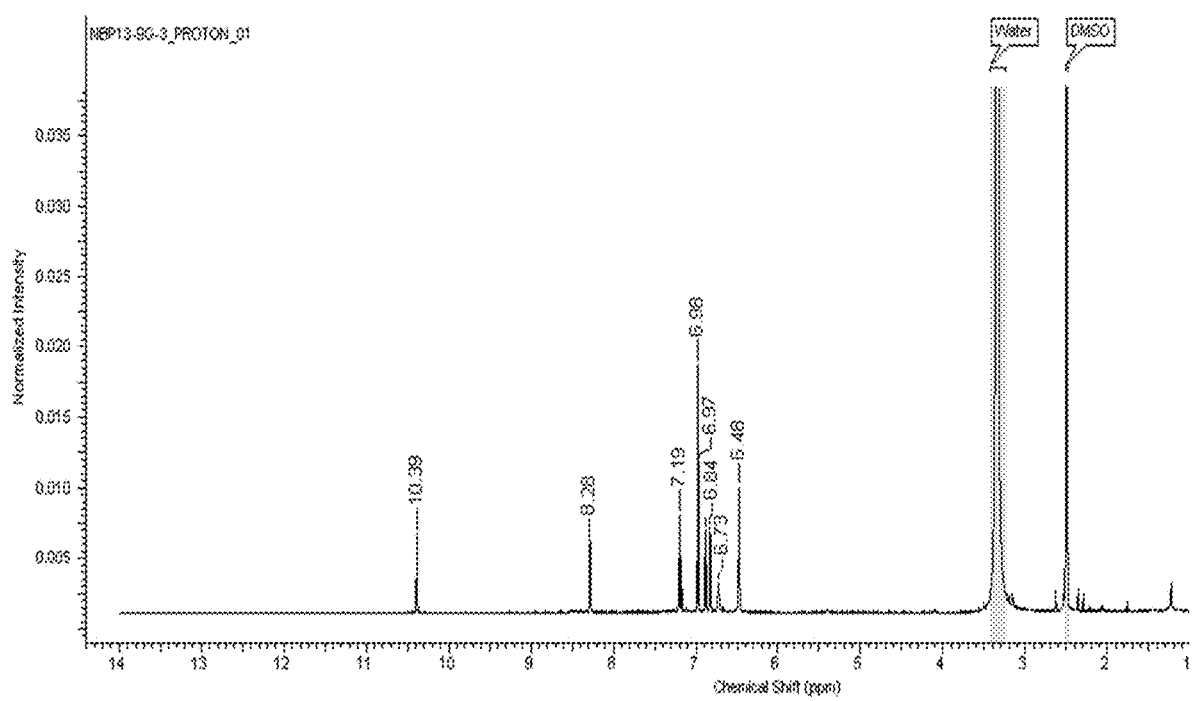
FIG. 11M is a graph showing $^1$H NMR spectra (500 MHz, DMSO-$d_6$) of Australindolone A (1) from fraction NBP13-9G-3.
Figure 11N:
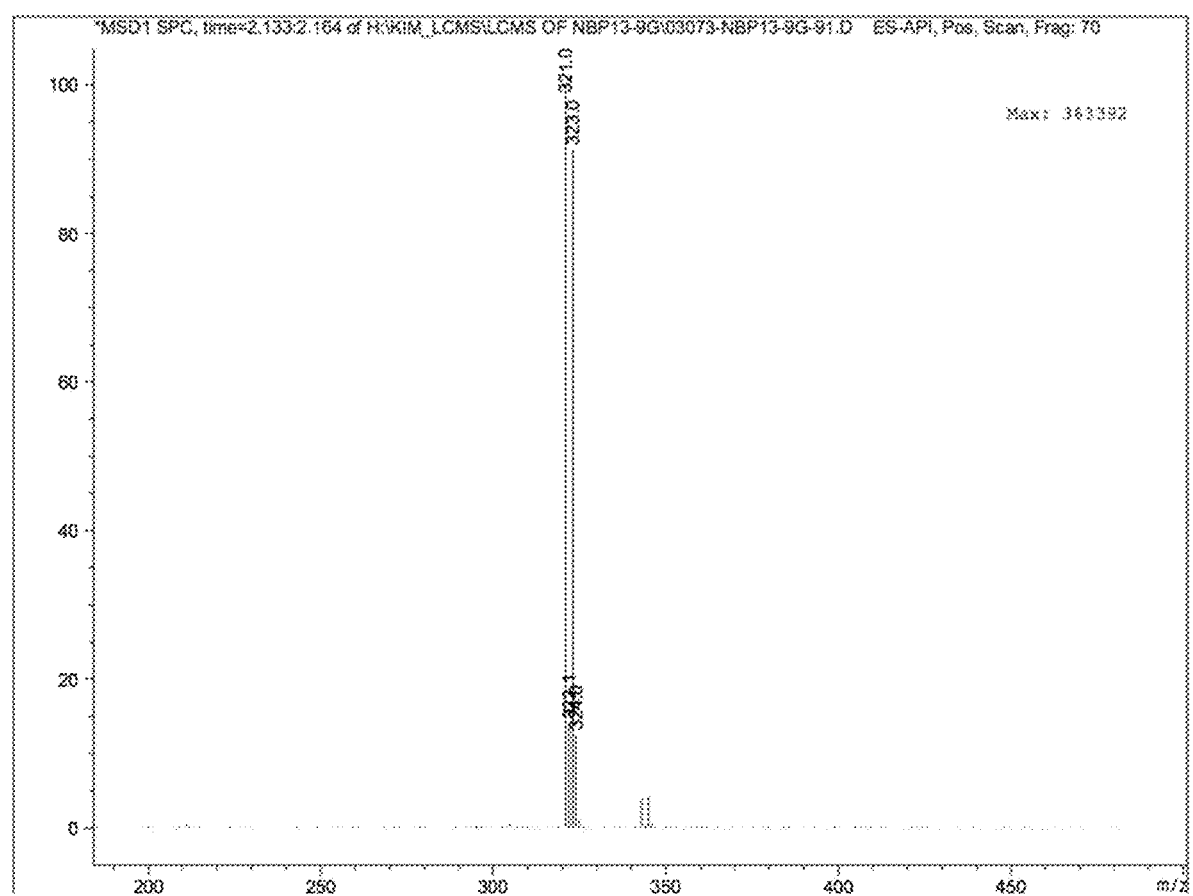
FIG. 11N is a graph showing ESIMS of Australindolone C (3) from fraction NBP13-9G-9.
Figure 11O:
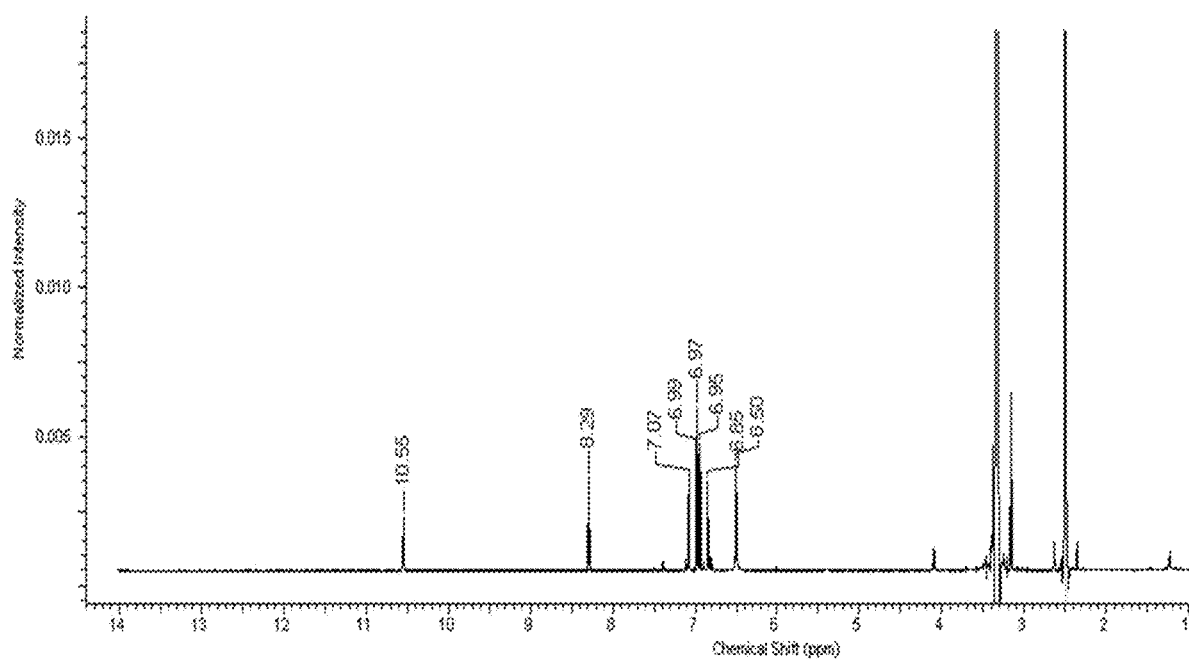
FIG. 11O is a graph showing $^1$H NMR spectra (500 MHz, DMSO-$d_6$) of Australindolone C (3) from fraction NBP13-9G-9.
Figure 11P:
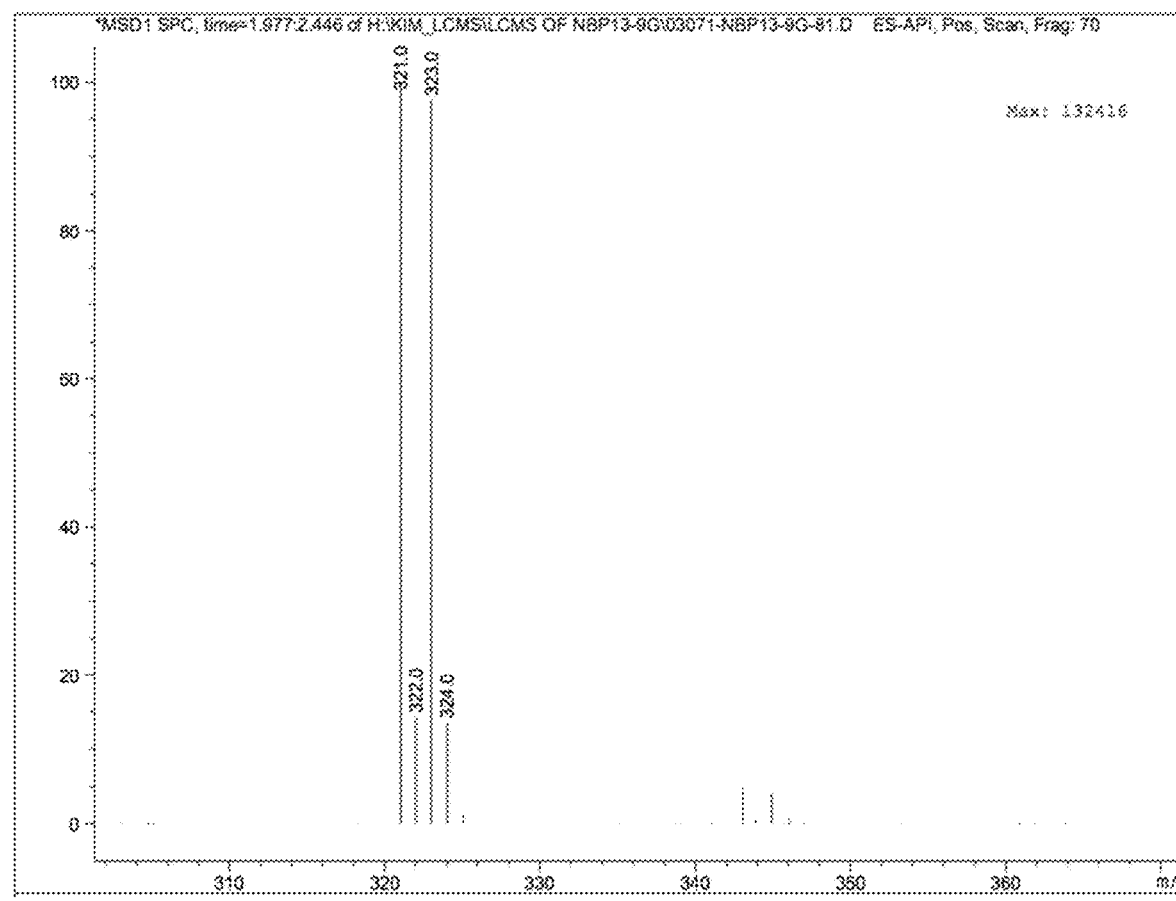
FIG. 11P is a graph showing ESIMS of fraction NBP13-9G-8.
Figure 11Q:
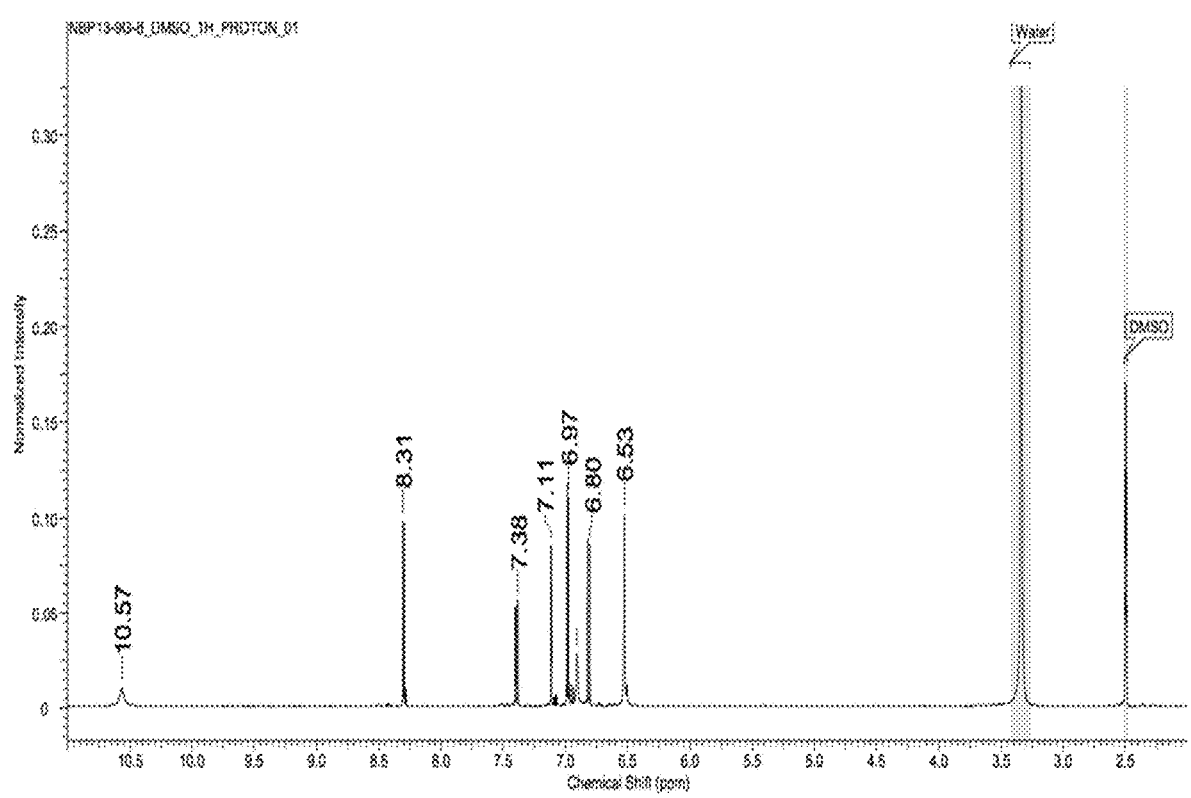
FIG. 11Q is a graph showing $^1$H NMR spectra (500 MHz, DMSO-$d_6$) of Australindolone B (2) from fraction NBP13-9G-8.
Figure 11R:
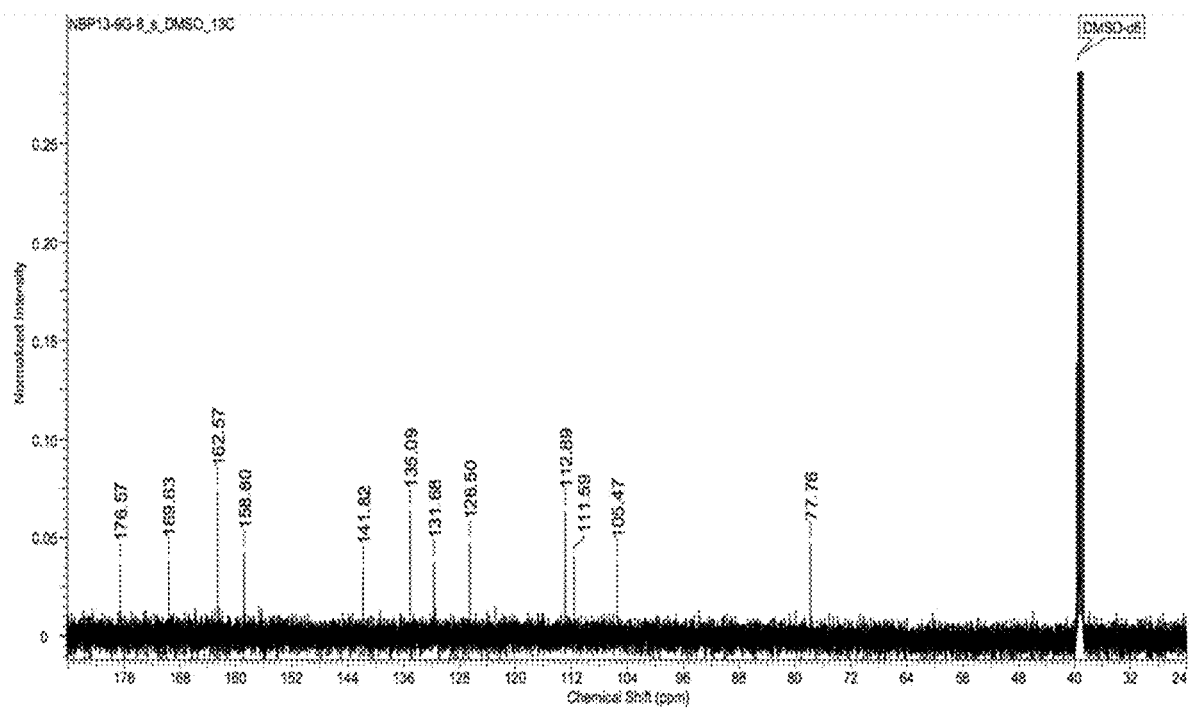
FIG. 11R is a graph showing $^{13}$C NMR spectra (500 MHz, DMSO-$d_6$) of Australindolone B (2) from fraction NBP13-9G-8.
Figure 11S:
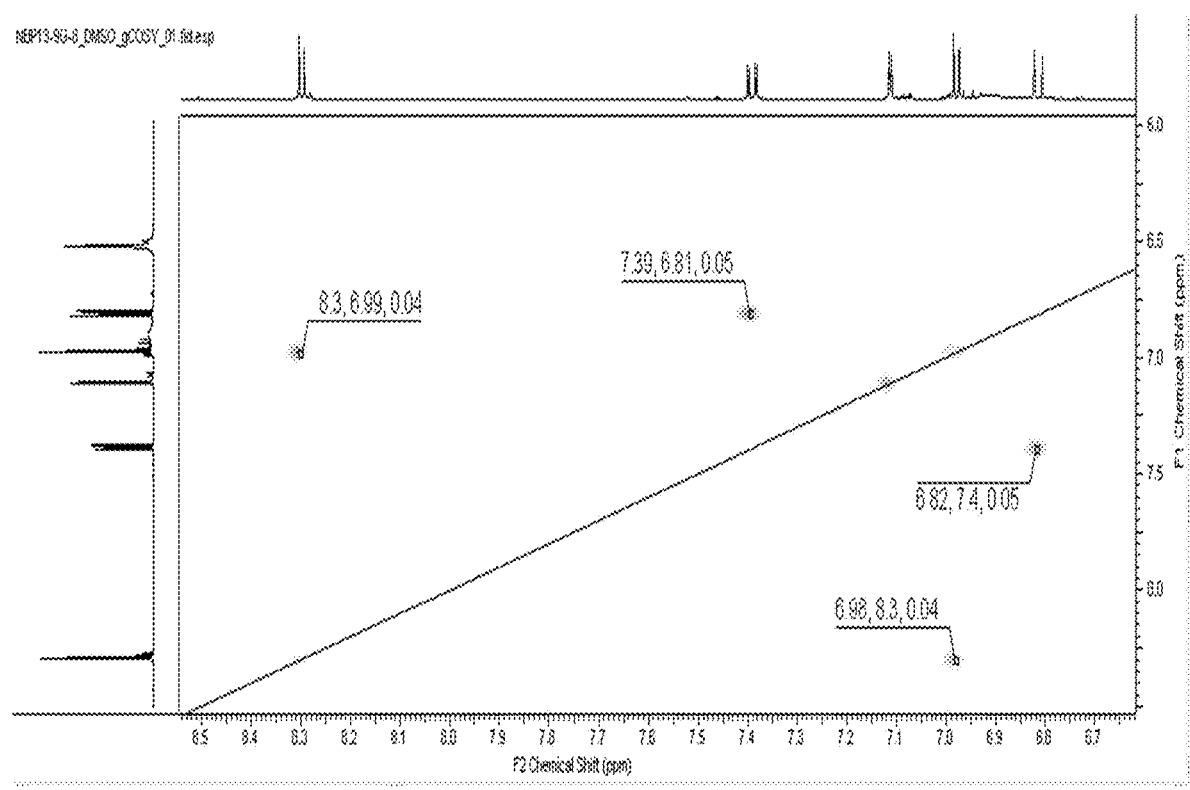
FIG. 11S is a graph showing gCOSY NMR spectra (500 MHz, DMSO-$d_6$) of Australindolone B (2) from fraction NBP13-9G-8.
Figure 11T:
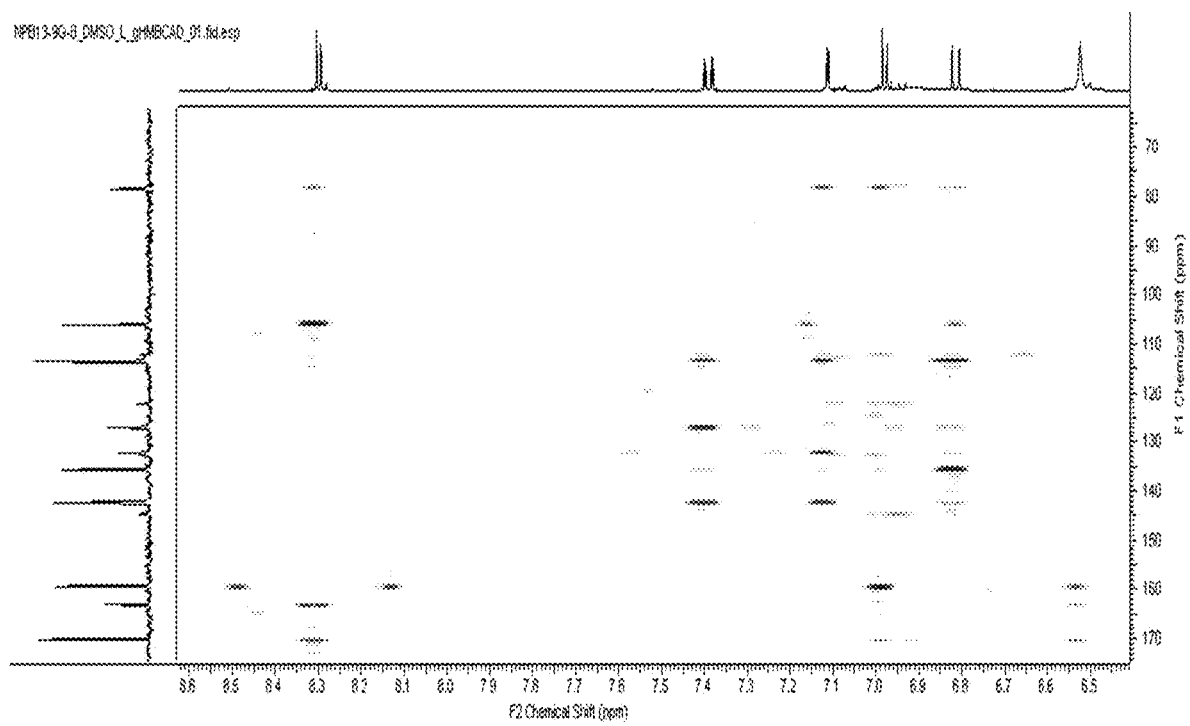
FIG. 11T is a graph showing gHMBC spectra (500 MHz, DMSO-$d_6$) of Australindolone B (2) from fraction NBP13-9G-8.
Figure 11U:
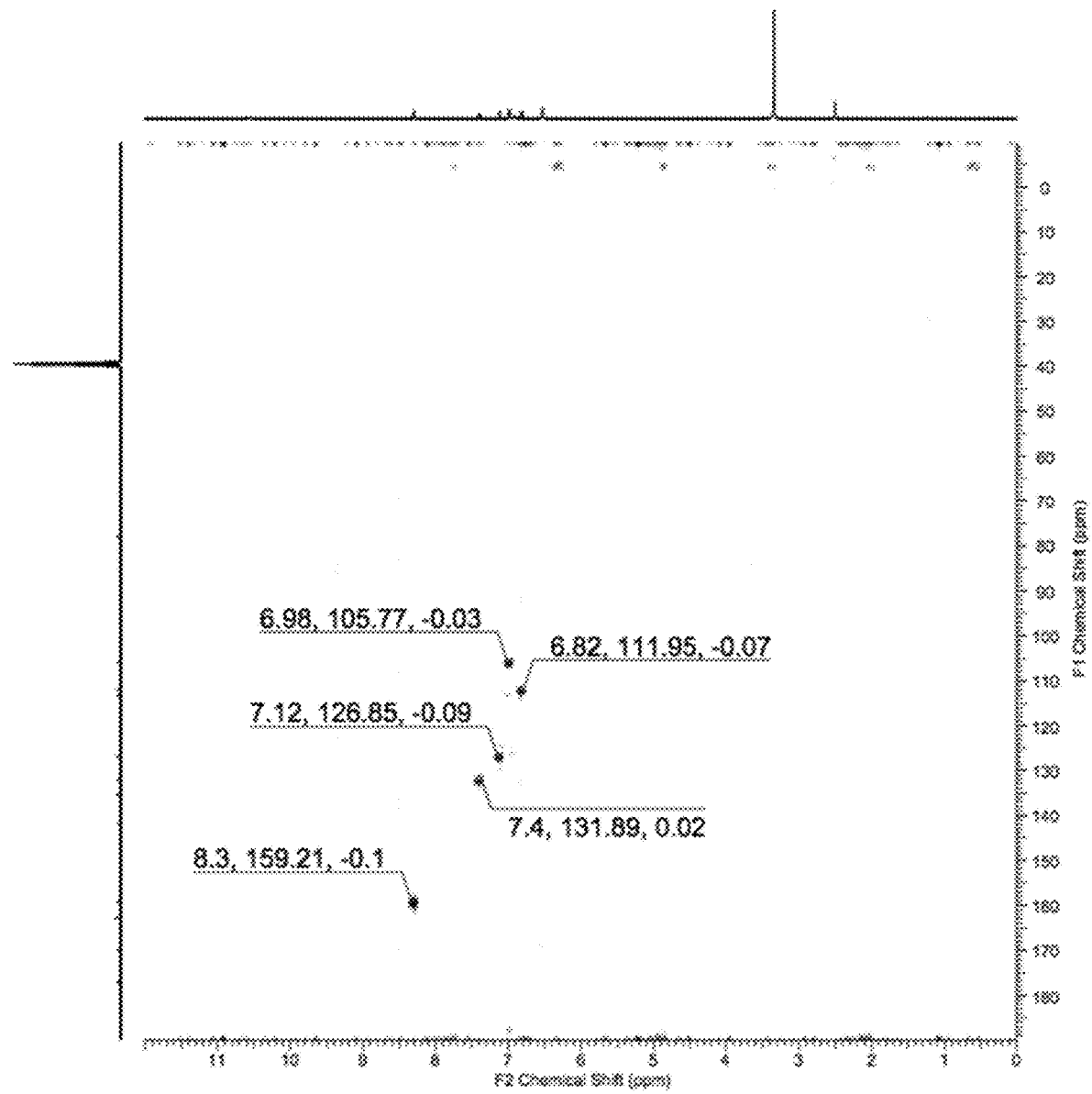
FIG. 11U is a graph showing gHSQC NMR spectra (500 MHz, DMSO-$d_6$) of Australindolone B (2) from fraction NBP13-9G-8
Figure 11V:
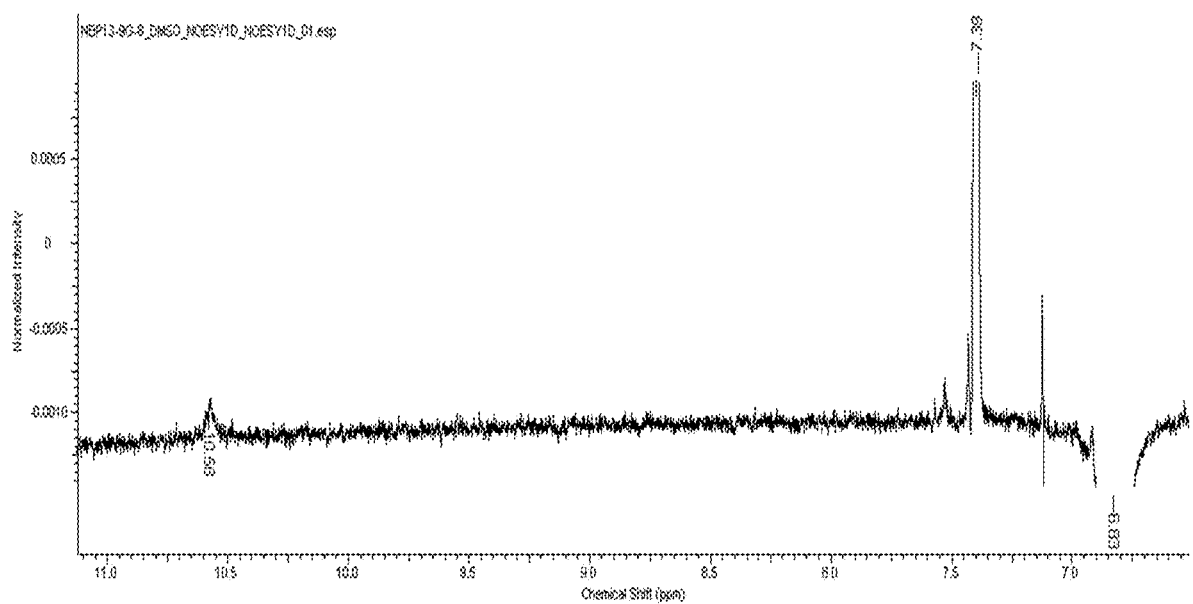
FIG. 11V is a graph showing 1D-NOESY spectra (500 MHz, DMSO-$d_6$) of Australindolone B (2) from fraction NBP13-9G-8.
Figure 12:
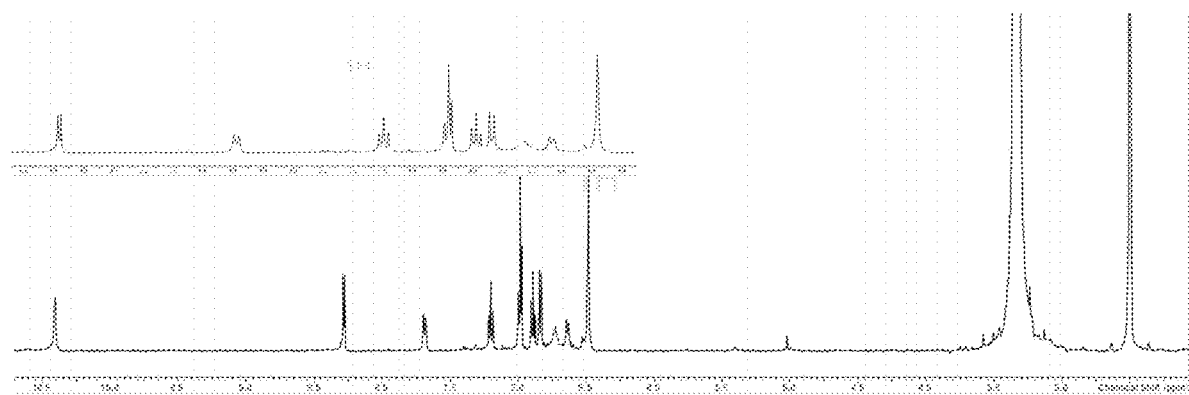
FIG. 12 is a graph depicting NMR of Australindolone A in DMSO-$d_6$. The key differences from the meridianin skeleton are evident in the loss of the aromatic amine and the H-3 proton, as well as the presence of the hydroxyl group.

Upon inspection of the initial $^1$H NMR and the ESIMS data of sub-fraction NBP13-9G-8, it was recognized that the peak and mass of this particular compound are not correlating to any of the known meridianins. Consequently, a full data set (gCOSY, gHMBC, gHSQC, and 1D-NOESY) was performed on the fraction to facilitate structure elucidation, seen in FIGS. 11A-V. Comparison and analysis of $^1$HNMR and ESIMS data of the fraction with fractions NBP13-9G-3 and NBP13-9G-9 also helped guiding structure elucidation of these fractions.

Figure 5:
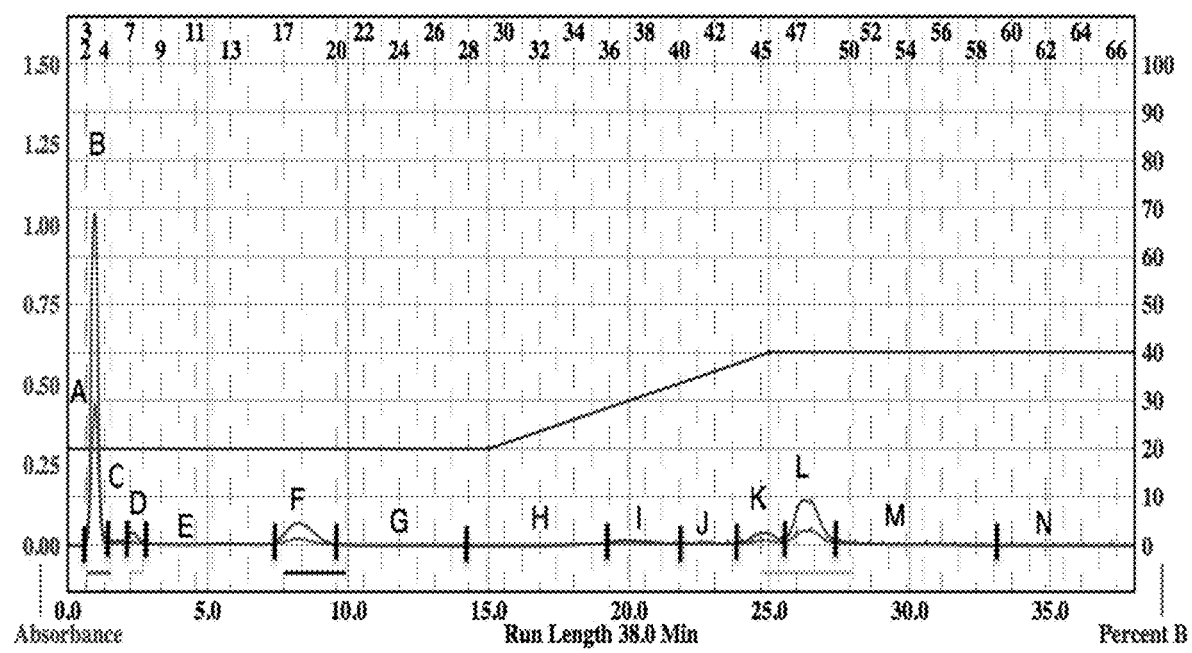
FIG. 5 is graph showing MPLC chromatogram collection scheme of fraction NBP13-9H.

MPLC reversed-phase was performed on fraction H due to its large amount of material. The run was set up using a Teledyne Isco Combi-Flash Rf Instrument and a RediSep C18 50 g Gold Chromatography Column. The run started off with 5% of Acetonitrile and 95% of water to a slow increase of 10% Acetonitrile and 90% of water over 45 minutes and followed by a rapid increase to 100% ACN in 10 minutes. Meanwhile, a wash of 100% ACN over 10 minutes was added as the concluding step, seen in FIG. 5. 14 sub-fractions were collected from the run, and $^1$H NMR data revealed that sub-fractions M and N contains possible meridianin C and D. Thus, HPLC was performed on both sub-fractions to isolate meridianin C and D, respectively. The fractionation scheme was constructed based on the mentioned collection methods, seen in FIG. 6.

Once the structures of the Meridianins were elucidated, a number of synthetic methods may be used to synthetically construct the Meridianins for use in the pharmaceutical compositions described herein. Such synthetic methods include, but are not limited to those contained in Walker, S. R.; J. C. Chem. Rev. 2009, 109, 3080, herein incorporated by reference into this disclosure.

Example 2—Identification of Meridianin A-E

The identities of isolated Meridianin A-E were confirmed by comparing 1D-NMR data to literature values, seen in Table 1-6. ESIMS was also used to reassure the identification. HRMS data was also assessed for Meridianin E, seen in FIGS. 11I-K. Minor differences between measured values and literature values are expected due to the differences in equipment. The literature values were obtained using a Bruker AC-200 MHz spectrometer, while a Varian 500 MHz cold-probe-equipped spectrometer was used to obtain the measured values.

TABLE 1

$^1$H NMR (500 MHZ, DMSO-$d_6$) data comparison table of Meridianin A from NBP13-9G-11.

| Position | $\delta_H$ (int., mult., Hz) | $\delta$ (int., mult., Hz)[4] | $\Delta\delta$ |
|---|---|---|---|
| N1-H | 11.77 (brs) | 11.71 (brs) | 0.06 |
| 2 | 8.25 (d, 0.6) | 8.20 (d, 1.2) | 0.05 |
| 4-OH | 13.60 (1H, s) | 13.55 (s) | 0.05 |
| 5 | 6.38 (dd; 7.8, 0.7) | 6.36 (dd; 7.1, 0.7) | 0.02 |
| 6 | 6.99 (dd; 7.8, 7.8) | 6.96 (dd; 7.1, 7.5) | 0.03 |
| 7 | 6.81 (dd; 8.2, 0.7) | 6.78 (dd; 7.5, 0.7) | 0.03 |
| 2'-NH$_2$ | 6.75 (2H, s) | 6.69 (s, 2H) | 0.06 |
| 5' | 7.13 (d; 5.3) | 7.09 (d, 5.4) | 0.04 |
| 6' | 8.13 (5.3) | 8.10 (d, 5.4) | 0.03 |

TABLE 2

$^1$H NMR (500 MHZ, DMSO-$d_6$) data comparison table of Meridianin B from NBP13-9G-18.

| Position | $\delta_H$ (int., mult., Hz) | $\delta$ (int., mult., Hz)[4] | $\Delta\delta$ |
|---|---|---|---|
| N1-H | 11.91 (s) | 11.99 (s) | 0.08 |
| 2 | 8.28 (d, 0.8) | 8.32 (d; 2.8) | 0.04 |
| 4-OH | 13.93 (s) | 13.92 (s) | 0.01 |
| 5 | 6.51 (d, 1.8) | 6.54 (d; 1.5) | 0.03 |
| 7 | 7.00 (d, 1.6) | 7.02 (d; 1.5) | 0.02 |
| 2'-NH$_2$ | 6.85 (2H, s) | 7.02 (s; 2H) | 0.27 |
| 5' | 7.14 (d, 5.6) | 7.18 (d; 5.5) | 0.04 |
| 6' | 8.17 (d, 5.6) | 8.17 (d; 5.5) | 0 |

TABLE 3

$^1$H NMR (500 MHZ, DMSO-$d_6$) data comparison table of Meridianin C from NBP13-9H-M-3.

| Position | $\delta_H$ (int., mult., Hz) | $\delta$ (int., mult., Hz)[4] | $\Delta\delta$ |
|---|---|---|---|
| N1-H | 11.95 (brs) | 11.85 (brs) | 0.1 |
| 2 | 8.24 (d, 0.5) | 8.24 (d; 2.5) | 0 |
| 4 | 8.74 (d, 1.96) | 8.75 (brd; 1.8) | 0.01 |
| 6 | 7.28 (dd, 8.31, 1.9) | 7.28 (dd; 8.4, 1.8) | 0 |
| 7 | 7.4 (d, 8.31) | 7.41 (d; 8.4) | 0.01 |
| 2'-NH$_2$ | 6.47 (2H, s) | 6.48 (s; 2H) | 0.01 |
| 5' | 6.99 (d, 5.38) | 7.00 (d; 5.5) | 0.01 |
| 6' | 8.09 (d, 5.38) | 8.11 (d; 5.5) | 0.02 |

TABLE 4

$^1$H NMR (500 MHZ, DMSO-$d_6$) data comparison table of Meridianin D from NBP13-9H-N-4.

| Position | $\delta_H$ (int., mult., Hz) | $\delta$ (int., mult., Hz)[4] | $\Delta\delta$ |
|---|---|---|---|
| N1-H | 11.86 (brs) | 11.76 (brs) | 0.1 |
| 2 | 8.26 (d, 0.6) | 8.21 (d; 2.6) | 0.05 |
| 4 | 8.75 (d, 2) | 8.55 (d; 8.4) | 0.2 |
| 5 | 7.29 (dd, 8.8, 1.9) | 7.24 (dd; 8.4, 1.8) | 0.05 |
| 7 | 7.4 (d, 8.3) | 7.63 (d; 1.8) | 0.23 |
| 2'-NH$_2$ | 6.49 (2H, s) | 6.43 (s; 2H) | 0.06 |
| 5' | 7.00 (d, 5.38) | 7.00 (d; 5.1) | 0 |
| 6' | 8.10 (d, 4.89) | 8.12 (d; 5.1) | 0.02 |

TABLE 5

$^1$H NMR (500 MHZ, DMSO-$d_6$) data comparison table of Meridianin E from fraction NBP13-9G-17.

| Position | $\delta_H$ (int., mult., Hz) | $\delta$ (int., mult., Hz)[4] | $\Delta\delta$ |
|---|---|---|---|
| N1-H | 11.91 (brs) | 11.86 (brs) | 0.05 |
| 2 | 8.31 (brs) | 8.29 (brs) | 0.02 |
| 4-OH | 13.89 (s) | 13.89 (s) | 0 |
| 5 | 6.37 (d, 8.31) | 6.37 (d; 8.3) | 0 |
| 6 | 7.19 (d, 8.3) | 7.19 (d; 8.3) | 0 |
| 2'-NH$_2$ | 6.85 (2H, s) | 6.79 (s; 2H) | 0.06 |
| 5' | 7.24 (d, 5.38) | 7.23 (d; 5.4) | 0.01 |
| 6' | 8.18 (d, 5.30) | 8.19 (d; 5.4) | 0.01 |

TABLE 6

$^{13}$C NMR (500 MHZ, DMSO-$d_6$) data comparison table of Meridianin E from fraction NBP13-9G-17.

| Position | $\delta_H$ (int., mult., Hz) | $\delta$ (int., mult., Hz)[4] | $\Delta\delta$ |
|---|---|---|---|
| 2 | 129.2 | 129.2 | 0 |
| 3 | 116.0 | 116.1 | 0.1 |

TABLE 6-continued

¹³C NMR (500 MHZ, DMSO-d₆) data
comparison table of Meridianin E from fraction NBP13-9G-17.

| Position | $\delta_H$ (int., mult., Hz) | $\delta$ (int., mult., Hz)[4] | $\Delta\delta$ |
|---|---|---|---|
| 3a |  | 115.0 | 115.2 | 0.2 |
| 4 |  | 151.8 | 152.0 | 0.2 |
| 5 |  | 107.1 | 107.3 | 0.2 |
| 6 |  | 126.7 | 126.7 | 0 |
| 7 |  | 92.5 | 92.6 | 0.1 |
| 7a |  | 136.8 | 136.9 | 0.1 |
| 2' |  | 160.0 | 160.2 | 0.2 |
| 4' |  | 161.6 | 161.8 | 0.2 |
| 5 |  | 104.7 | 104.8 | 0.1 |
| 6' |  | 158.9 | 159.0 | 0.1 |

Example 3—Australindolones A-D (1-4) and Meridianin H (12)

*Synoicum* sp. was collected by trawling at 220 m on the Scotia Arc of the Southern Ocean. Using previously reported isolation methods, the $CH_2Cl_2$/MeOH extract of the freeze-dried organism was subjected to reversed-phase chromatography and yielded five new compounds, australindolone A (1, 2.0 mg), australindolone B (2, 4.0 mg), australindolone C (3, 1.0 mg), australindolone D (4, 1.0 mg), and meridianin H (12, 2.0 mg) eluting in 15% methanol in water, alongside the seven known meridianins (5-11). Final purification was achieved with an acetonitrile/water gradient on HPLC.

General Experimental Procedures

An Autopol IV polarimeter was used to measure the optical rotation at 589 nm. IR spectra were measured using an Agilent Technologies Cary 630 FTIR. UV spectra were measured using an Agilent Technologies Cary 60 UV-vis spectrophotometer. A Varian Innova 500, Varian Direct Drive 500, or Varian Innova 400 MHz NMR spectrometer at 298K was used to record the NMR spectra. The NMR spectra are recorded using as reference the residual shifts of DMSO ($\delta_H$ 2.50 ppm and $\delta_C$ 39.51 ppm). The high-resolution mass spectra were recorder on an Agilent Technologies LC/MS ToF electrospray ionization spectrometer. MPLC was carried as direct injections on a redisept C18 50 g flash column using a Teledyne Isco Combiflash Rf200i, equipped with an evaporative light scattering detector. HPLC was performed using a preparative YMC-Pack ODS RP column (250×20 mm) and analytical C-18 columns (250×10 mm) on a LC-20AD Shimadzu system and an SPD-20A UV detector.

Animal Material

The yellow tunicate *Synoicum* sp. was collected at a depth of 200m from near Shag Rocks islands and South Georgia in *Antarctica* and stored at −20° C. until it was analyzed. The organism was identified by Dr Linda Cole of the Smithsonian National Museum of Natural Sciences.

Frozen *Synoicum* spp. was lyophilized, and 200 g of dry organism were extracted using 1:1 $CH_2Cl_2$/MeOH for three days. The extract was dried down on a rotary evaporator, and the residue was partitioned between hexane and 95% aqueous MeOH to remove any non-polar components. The aqueous layer was concentrated and further partitioned between EtOAc and $H_2O$ to remove salts. The EtOAc layer was dried and the 2 g of crude extract were subjected to medium pressure liquid chromatography with a $H_2O$/MeOH gradient, which gave 7 fractions. Further purification was performed on HPLC using 5-100% $H_2O$/MeCN and a C-18 analytical column, to afford australindolones A (1), B (2), C (3) and D (4), meridianin H (12), and the known meridianins A-G (5-11).

Australindolone A: $[\alpha]_D^{21}$ −10.1; UV (MeOH) $\lambda_{max}$ 213, 297 nm; HR ESIMS (+) m/z 243.0877 ($C_{12}H_{11}N_4O_2$ calculated 243.2409); ¹H and ¹³C NMR, see table 7

Australindolone B: $[\alpha]_D^{21}$ 30.2; UV (MeOH) $\lambda_{max}$ 211, 297 nm; HR ESIMS (+) m/z 320.9951 ($C_{12}H_{10}BrN_4O_2$ calculated 320.9987); ¹H and ¹³C NMR, see table 10

Australindolone C: $[\alpha]_D^{21}$ −20.1; UV (MeOH) $\lambda_{max}$ 218, 303 nm; HR ESIMS (+) m/z 320.9944 ($C_{12}H_{10}BrN_4O_2$ calculated 320.9987); ¹H and ¹³C NMR, see table 10

Australindolone D: $[\alpha]_D^{21}$ −30.2; UV (MeOH) $\lambda_{max}$ 223, 298 nm; HR ESIMS (+) m/z 398.9083 ($C_{12}H_9Br_2N_4O_2$ calculated 398.9092); ¹H and ¹³C NMR, see table 12

Meridianin H: UV (MeOH) $\lambda_{max}$ 223, 350 nm; HR ESIMS (+) m/z 382.9129 ($C_{12}H_9Br_2N_4O$ calculated 382.9143); ¹H and ¹³C NMR, see table 13

Australindolone A (1)

Australindolone A (1) was isolated as a yellow solid. The HRESIMS showed a molecular formula of $C_{12}H_{10}N_4O_2$ ([M+H]⁺: 243.0866, calculated 243.0803, Δ=1.6 amu), which was supported by ¹H and ¹³C NMR data. The exchangeable in $D_2O$ broad singlet at 6.74 ppm indicated the presence of an alcohol. The ¹³C NMR shift at 177.4 ppm strongly suggested the presence of an amide, further supported by the singlet at 10.41 ppm and the molecular formula. The degree of unsaturation of the compound, as well as the remaining ¹³C NMR shifts pointed to the presence of two heteroaromatic rings. The spin system of C-5' and C-6' was built using the COSY correlations. The HMBC data connecting H-6' at $\delta_H$ 8.26 ppm to C-2' at $\delta_C$ 162.9 ppm as well as the shift itself of C-2' and the broad singlet at 6.78 (2H), helped to piece together the 2-amino-pyrimidine ring. This partial structure was supported by the literature data observed in the meridianins. (Franco, L. H.; Joffé, E. B. de K.; Puricelli, L.; Tatian, M.; Seldes, A. M.; Palermo, J. A. Indole Alkaloids from the Tunicate *Aplidium meridianum*. *Journal of Natural Products* 1998, 61 (9), 1130-1132).

Figure 13:
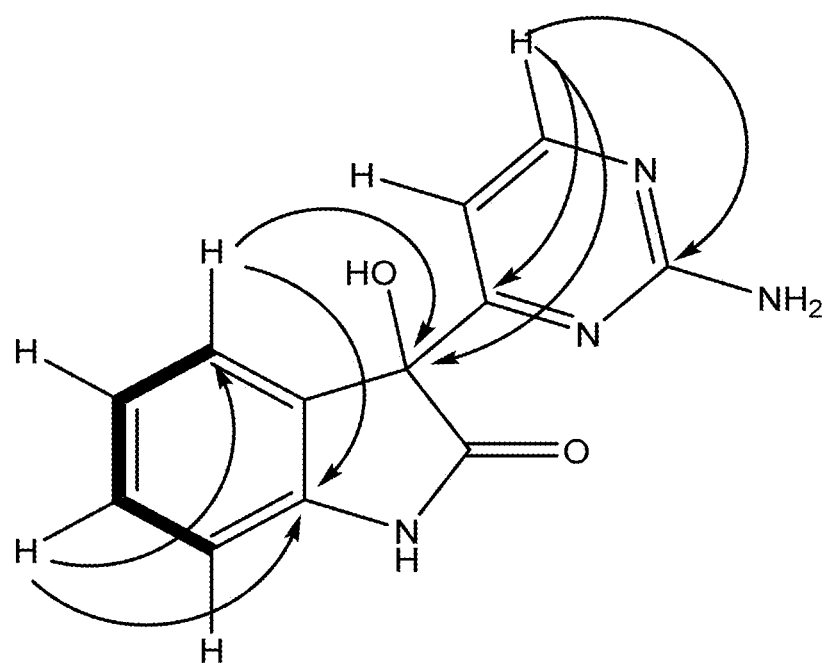
FIG. 13 is an image depicting Key COSY (bold) and HMBC (arrows) Correlations for Australindolone A.

The data obtained from the COSY NMR helped build the spin system of the protons H-4, H-5, H-6, and H-7, forming the aromatic ring. The HMBC data furthered expanded the ring by indicating the position of the alcohol based on the correlation with the proton on C-4 and C-6' respectively. The ¹³C values at $\delta_C$ 78.1 ppm indicated the position of the hydroxyl group. The HMBC correlation of H-1 at $\delta_H$ 10.41 ppm to the alcohol baring C-3, combined with the $\delta_C$ 177.4 ppm value of C-2, indicating the presence of either an ester or an amide, assisted in closing the ring and forming the indolone skeleton. (see FIG. 13). The structure was further supported by the UV and IR data obtained. A C═O peak at 1640 cm⁻¹, as well as a broad peak characteristic of alcohols and primary amines at 3300-3500 cm⁻¹, confirmed the presence of the amide, as well as the presence of the amine and the alcohol.

TABLE 7

NMR Spectroscopic Data for Australindolone A (1)[a]

| | Australindolone A (1) | | |
|---|---|---|---|
| Position | $\delta_C$[b] | $\delta_H$[c] | HMBC |
| 1 NH |  | 10.41 (s) | 3 |
| 2 | 177.4, C |  |  |
| 3 | 78.1, C |  |  |
| 3-OH |  | 6.74 (1H, brs) |  |
| 3a | 133.1, C |  |  |
| 4 | 124.1, C | 6.99 (1H, d, 7.2) | 3, 6, 7a |

TABLE 7-continued

NMR Spectroscopic Data for Australindolone A (1)[a]

| | Australindolone A (1) | | |
|---|---|---|---|
| Position | $\delta_C$[b] | $\delta_H$[c] | HMBC |
| 5 | 121.6, C | 6.89 (1H, dd, 7.5, 7.5) | 3a, 7 |
| 6 | 129.4, C | 7.2 (1H, dd, 7.5, 7.5) | 4, 7a |
| 7 | 109.8, CH | 6.84 (1H, d, 7.7) | 3a, 5 |
| 7a | 142.8, C | | |
| 1' | | | |
| 2 | 162.9, C | | |
| 2'-NH$_2$ | | 6.48 (2H, brs) | 2', 5', 6' |
| 3' | | | |
| 4' | 170.6, C | | |
| 5' | 105.8, CH | 6.97 (1H, d, 5.1) | 3, 6' |
| 6' | 158.9, CH | 8.28 (1H, d, 5.1) | 2', 4', 5' |

[a]DMSO;
[b]125 MHz, multiplicity (from HSQC);
[c]400 MHZ (integration, multiplicity, J (Hz))

Figure 9:
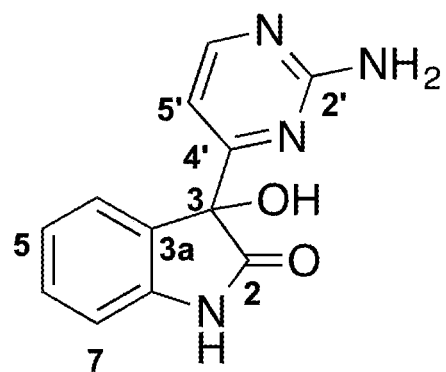
FIG. 9 is an illustration of the structure of isolated compound from fraction NBP13-9G-3.

Initial $^1$H NMR data of fraction NBP13-9G-3 illustrated similarities as those of fraction NBP13-9G-8. The key similarity is the proton peaks at position 2'-NH$_2$, 5', and 6' of the compound, which are the inherent indicators of a 3-aminopyrimidine backbone. Further multiplicity and integration analysis and comparison to those of meridianin A-E proved that the hypothesis is correct. Additionally, the broad singlet $\delta_H$ 10.39 indicated that the compound also shares the common backbone of bromoanaindolone with NBP13-9G-8 (Table 8). However, an additional $^1$H NMR peak, the lack of a bromine pattern and smaller ESIMS observable mass reveal that the compound, unlike NBP13-9G-8, is not at all Bromine substituted. Therefore, the structure of NBP13-9G-3 can be structured as having as having 3-hydroxyindolin-2-one backbone, which is the un-substituted derivative or bromoanaindolone, as seen in FIG. 9 (corresponding to Australindolone A (1)).

TABLE 8

$^1$H NMR (500 MHZ, DMSO-d$_6$) data of fraction NBP13-9G-3.

| Position | $\delta_H$ (int., mult., Hz) |
|---|---|
| 1-NH | 10.39 (brs) |
| 6' | 8.29 (d, 4.9) |
| 5 or 6 | 7.20 (td, 7.8, 7.8, 1.3) |
| 4 or 7 | 6.98 (dd ,7.8) |
| 5' | 6.97 (d, 4.9) |
| 5 or 6 | 6.89 (td, 7.6, 7.6, 1.0) |
| 4 or 7 | 6.83 (d, 7.8) |
| 3-OH | 6.73 (brs) |
| 2'-NH$_2$ | 6.48 (2H, brs) |

Australindolone B (2)

Figure 14:
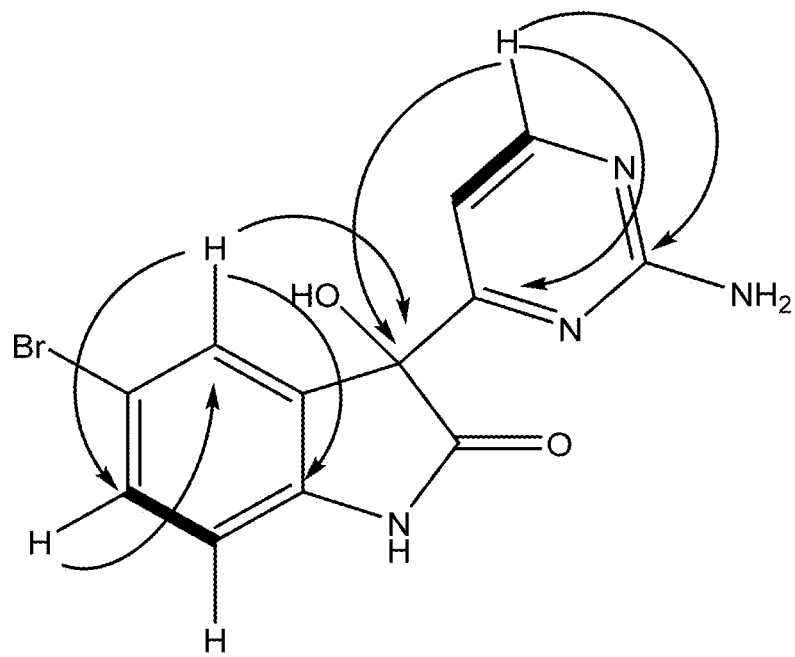
FIG. 14 is an image depicting Key COSY (bold) and HMBC (arrows) Correlations for Australindolone B.

Australindolone B (2) was also isolated as a yellow solid. The HRESIMS of 2 established a molecular formula of C$_{12}$H$_9$N$_4$O$_2$Br ([M+H]$^+$: 320.9951, calculated 320.9987, Δ=1.6 amu). Based on the $^1$H NMR spectrum (Table 3), the compound showed a similar skeleton to australindolone A (1), perhaps derivatized by the addition of a bromine atom. Two meta-oriented protons, at $\delta_H$ 7.12 (d, J=2 Hz), $\delta_H$ 7.39 (dd, J=8.2 Hz, 2.1 Hz) and two ortho-oriented protons, at $\delta_H$ 7.39 (dd, J=8.2 Hz, 2.1 Hz) and $\delta_H$ 6.91 (d, J=8.2 Hz), suggested the indole ring seen in structure 1 was monosubstituted. This coupling pattern indicated the presence of the bromine in either position C-5 or C-6. The downfield shift of H-4 combined with the downfield shift of the 3-OH established that the bromine was in position C-5. Further, the downfield shift of C-3a combined with the downfield shift of C-4, strengthened the positioning of the Br on C-5. (FIG. 14)

When looking at both $^1$H and $^{13}$C NMR spectrums of NBP13-9G-8 (Australindolone B (2)), several similarities and differences were recognized when comparing to the NMR data of the known meridianins. The number of protons and carbons that can be seen on NMR data is similar to those that share Meridianin skeleton. Another key similarity is the proton peaks $\delta_H$ 6.53, $\delta_H$ 6.98, and $\delta_H$ 8.30 of the compound (Table 9). These particular peaks are the key indicators of a 3-aminopyrimidine backbone, and can be seen to share the same multiplicity and integration throughout meridianin A-E. Consequently, these inherent peaks were aiding to the suspicion that the compound shares a 3-aminopyrimidine backbone as with the other meridianins. Correlation between the 5'-proton and the 6'-proton is also observed using gCOSY, and thus further confirm that a 3-aminopyrimidine backbone is present, seen in FIG. 7.

However, there are two $^{13}$C peaks that were different when comparing to those of previously found Meridianins. $\delta_C$ 176.57 and $\delta_C$ 77.76 do not correlate to any of the known Meridianins $^{13}$CNMR data. Thus, these peaks served as the initial indications of a structure adjustment to the original indole skeleton. To facilitate structure elucidation, a chemical formula was determined by comparing ESIMS, NMR data and literature knowledge.

TABLE 9

NMR data (500 MHZ, DMSO-d$_6$) of fraction NBP13-9G-8 (Australindolone B (2)).

| Position | $\delta_H$ (int., mult., Hz) | $\delta_C$ | gHMBC |
|---|---|---|---|
| N1-H | 10.57 (br · s) | | |
| 3-OH | 6.91 (br · s) | 78.1 | 170.0 |
| 4 | 7.11 (d, 2.1) | 126.8 | 142.1, 135.4, 132, 113.2, 111.9, 78.1 |
| 5 | | 113.2 | |
| 6 | 7.39 (dd, 8.2, 1.9) | 132.0 | 142.1, 126.8, 113.2, 135.4 |
| 7 | 6.82 (d, 8.2) | 111.9 | 142.1, 135.4, 132, 126.8, 113.1, 78.1 |
| 2'-NH2 | 6.53 (2H, br · s) | | 170.0, 162.9, 159.1 |
| 4' | | 170.0 | |
| 5' | 6.98 (d, 4.9) | 105.8 | 176.9, 170.0, 159.1, 135.4, 78.1 |
| 6' | 8.30 (d, 4.9) | 159.1 | 170.0, 162.9, 105.8, 78.1 |
| 3a | | 135.4 | |
| 7a | | 142.1 | |

By comparing both $^1$H and $^{13}$C data and ESIMIS, a chemical formula can be calculated. Due to similarity of the 3-aminopyrimidine backbone with other Meridianins and the ESIMS mass, an assumption that the compound has four nitrogen is deducible. Additionally, based on the shifting values of their corresponding $^{13}$C peaks, an assumption that the compound has a hydroxyl group and a carbonyl carbon is also deducible. Therefore, the chemical formula can be calculated by comparing such observation to the molecular weight from ESIMS. With 8 observable $^1$H peaks and 12 $^{13}$C peaks, a bromine and a hydroxyl substituent, and one carbonyl oxygen, the molecular weight can be calculated as roughly 320, which is also the value that can be observed from ESIMS. The finalized chemical formula is C$_{12}$H$_9$BrN$_4$O$_2$.

Coupling patterns on peaks $\delta_H$ 7.11 (d; 2.1), $\delta_H$ 7.39 (dd; 8.2, 1.9), and $\delta_H$ 6.82 (d; 8.2) can further highlight the structure (Table 9). It can be deduced that the protons on peak $\delta_H$ 7.11 and $\delta_H$ 7.39 are meta to each other due to their small J-coupling values. Meanwhile, peaks $\delta_H$ 7.39 and $\delta_H$ 6.82 are ortho to each other due to their larger J-coupling values. These coupling patterns can also be observed on NMR data of Meridianin C, which lead to an assumption that the inherent bromine is also substituted at 5-carbon[4]. From gHSQC, these proton peaks can be concluded as correlating to these respective carbon peaks: $\delta_C$ 132.0, Sc 111.9, and $\delta_C$ 126.8.

However, the position of $\delta_H$ 6.82 was inconclusive. With the ambiguous multiplicity and coupling factors, it can also be at the 4-C. gHMBC data on this particular peak is also inconclusive Consequently, 1D-NOESY was implemented to determine correlation of saturated proton with other protons that are close in space. Initially, the irradiate proton was chosen to the one of the amide group. However, due to its broadness, the data was deficient. The irradiate proton was then selected to be the $^1$H peak of 6.82 ppm. For this particular proton, the 1D-NOESY was able to show its correlation with $\delta_H$ 10.57, and $\delta_H$ 7.39. Therefore, based on 1D-NOESY data, $\delta_H$ 6.82 was confirmed to be at 7-position.

One interesting feature of this backbone is the gHMBC correlation between the 4'-C of 3-aminopyrimidine to a broad, singlet proton at 6.91 ppm. This is the only correlation that the proton has with any carbon and thus its assigned position is carefully examined. The lack of gHSQC correlation of this proton, the nature of its multiplicity and integration also indicated that the proton is attached to an oxygen. The small chemical shift of $\delta_H$ 6.91 and ESIMS data-derived chemical formula narrowed the possible attachment to a hydroxyl group. The small $\delta_C$ 78.1 also supported this assumption, seen in Table 9.

With one $^{13}$C peak of 176.9 ppm left to assign and a broad single $\delta_H$ 10.57, gHMBC correlation between this particular carbon peak and other protons was carefully analyzed. With only one gHMBC correlation with the 5'-H of the 3-aminopyrimidine backbone, the peak was assigned at the 2-position. At this position, the carbon can only correlate with one proton that is 4 bonds away. The singlet $\delta_H$ 10.57, on the other hand, does not have gHSQC or gHMBC. Additionally, the carbon also has no gHSQC correlation and along with ESIMS-derived chemical formula and its high NMR shifting value, both carbon and proton were determined to be those of an amide substituent. The indole backbone of previous meridianins was re-characterized into a bromoanaindolone. This particular scaffold was first extracted from the cyanobacterium *Anabaena constricta*. However, its attachment to a 3-aminopyrimidine skeleton has not yet been found. With these two scaffolds, the isolated compound from fraction NBP13-9G-8 can be structured as that seen in FIG. 8, corresponding to Australindolone B (2).

Australindolone C (3)

Australindolone C (3), a yellow solid like other members of this indolones family, displayed a molecular formula of $C_{12}H_9N_4O_2Br$ ([M+H]$^+$: 320.9944, calculated 320.9987, $\Delta$=4.3 amu), based on HRESIMS, $^1$H and $^{13}$C NMR data, indicating it is isomeric to 2. The coupling pattern of two ortho-oriented protons at 6.95 (d, J=7.8 Hz) ppm and 7.08 ppm (dd, J=8.1 Hz, 2 Hz) and two meta-oriented protons 7.08 ppm (dd, J=8.1 Hz, 2 Hz) and 6.99 ppm (d, J 2 Hz) indicated once again the presence of the bromine in either position C-5 or C-6. The upfield shift of the 3-OH compared to 2, combined with the upfield shift of H-4, indicates that the positioning of the Br is on C-6 instead of C-5. Further confirmation is given by the downfield shift of C-7a and upfield shift of C-3a, as well as the upfield shift of C-6 compared to compound 2.

TABLE 10

NMR spectroscopic data for australindolone B (2) and C (3)$^a$

| Position | Australindolone B (2) | | | Australindolone C (3) | | |
| --- | --- | --- | --- | --- | --- | --- |
| | $\delta_C{}^b$ | $\delta_H{}^c$ | gHMBC | $\delta_C{}^b$ | $\delta_H{}^c$ | HMBC |
| 1 NH | | 10.57 (1H, s) | | | 10.57 (1H, s) | 3, 3a |
| 2 | 176.9, C | | | 177.3, C | | |
| 3 | 78.1, C | | | 77.8, C | | |
| 3-OH | | 6.91 (1H, brs) | | | 6.85 (1H, brs) | |
| 3a | 135.4, C | | | 132.5, C | | |
| 4 | 126.8, CH | 7.12 (1H, d, 2.0) | 3, 5, 6, 7, 7a | 126.0, CH | 6.95 (1H, d, 7.8) | 3, 6, 7a |
| 5 | 113.2, C | | | 124.2, CH | 7.08 (1H, dd, 8.1, 2.0) | 3a, 6, 7 |
| 6 | 132.0, CH | 7.39 (1H, dd, 8.2, 2.1) | 3a, 4, 5, 7a | 121.8, C | | |
| 7 | 111.9, CH | 6.91 (1H, d, 8.2) | 3, 3a, 4, 5, 7a | 112.6, CH | 6.99 (1H, d, 2.0) | 5, 6, 7a |
| 7a | 142.6, C | | | 144.6, C | | |
| 1' | — | — | — | — | — | — |
| 2' | 162.9, C | | | 162.9, C | | |
| 2'-NH$_2$ | | 6.83 (2H, brs) | | | 6.51 (2H, brs) | |
| 3' | — | — | — | — | — | — |
| 4' | 170.0, C | | | 170.1, C | | |
| 5' | 105.8, C | 6.99 (1H, d, 5.1) | 3, 3a, 6, 7, 7a, 4' | 105.7, CH | 6.97 (1H, d, 4.9) | 6' |
| 6' | 159.1, C | 8.3 (1H, d, 5.1) | 3, 2', 4', 5' | 159.0, CH | 8.30 (1H, d, 4.9) | 4', 5' |

$^a$DMSO; $^b$125 MHz, multiplicity (from HSQC); $^c$400 MHz (integration, multiplicity, J (Hz))

Figure 10:
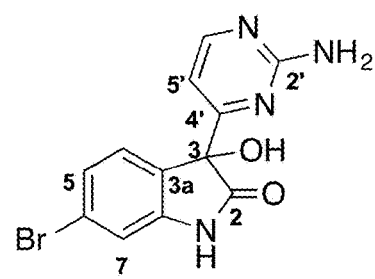
FIG. 10 is and image of the structure of isolated compound from fraction NBP13-9G-9.

Initial $^1$H NMR data of fraction NBP13-9G-9 also illustrates similarities as those of fraction NBP13-9G-8. The compound, along with NBP13-9G-8, exhibits proton peaks at position 2'-NH$_2$, 5', and 6', which are key indicators of 3-aminopyrimidine backbone. Just like NBP13-9G-8, the compound also has 9 observable $^1$H peaks, 12 $^{13}$C peaks on NMR, and the same ESIMS mass. A bromine pattern can also be observed from ESIMS data. Thus, a conclusion that NBP13-9G-9 shares the same chemical formula as NBP13-9G-8 is deducible. This key evidence indicates the NBP13-9G-9 is a structural isomer of NBP13-9G-8. Based on $^1$H NMR data and J-coupling values, $\delta_H$ 7.08 is ortho to $\delta_H$ 6.95 while meta to $\delta_H$ 6.99. Based on such information, there are only two positions that the Bromine can be substituted, on the 3-hydroxyindolin-2-one, that would allow the compound to exhibit such coupling and multiplicity: position 5 and position 6. NBP13-9G-8, another illustration of such pattern, further testify such statement. Therefore, comparison NMR data between fractions NBP13-9G-8 and NBP13-9G-9 can confirm the position of the substituted Bromine. With NBP13-9G-8, the bromine is affixed on the 5-carbon due to the gHMBC correlation between the 5-carbon with the 4-proton. The 4-proton, in return, is placed at that particular position due to its gHSQC correlation with 4-carbon and gHMBC correlation with 3a-, 3-, 7a, 6-, 7-, and 5-carbons. 1D-NOESY also showed correlations between $\delta_H$ 6.82 (7-H) and $\delta_H$ 10.57 (1-NH), $\delta_H$ 7.39 (6-H). Consequently, such data lead to a structure elucidation that exclusively places bromine at the 5-position. Therefore, through process of elimination, compound of fraction NBP13-9G-9 would have its bromine substituted at the 6-positon. The differences in shifting of fraction NBP13-9G-9 also confirm such hypothesis. $\delta_H$ 6.95 on 4-carbon of fraction NBP13-9G-9 slightly shifted upfield when comparing to the $\delta_H$ 7.11 of NBP13-9G-8 (Table 9 and Table 10). An explanation for such disparity is due to the change of position of bromine, an electron-withdrawing group, which lead to a loss of shielding by electron density and resulted in a downfield shift. The lack of bromine as a substitution on the 5-carbon lead to a shielded effect and resulted in an upfield shift of 4-proton, and a downfield shift on 7-proton. Thus, the structure of fraction NBP13-9G-9 can be illustrated as such seen in FIG. 10, corresponding to Australindolone C (3).

TABLE 11

$^1$H NMR (500 MHZ, DMSO-$d_6$) data of fraction NBP13-9G-9.

| Position | $\delta_H$ (int., mult., Hz) |
|---|---|
| 1-NH | 10.57 (brs) |
| 6' | 8.30 (d, 4.9) |
| 5 | 7.08 (dd, 8.1, 1.7) |
| 7 | 6.99 (d, 2.0) |
| 5' | 6.97 (d, 4.9) |
| 4 | 6.95 (d, 7.8) |
| 3-OH | 6.85 (brs) |
| 2'-NH2 | 6.51 (2H, brs) |

Due to the structures of NBP13-9G-3, NBP13-9G-8, and NBP13-9G-9 and their relations with the Meridianin family, the structures were named Australindolone A-C, respectively. Further structure analysis, such as X-ray crystallography and HRESIMS, is performed on the new isolated compounds. Full data set of NMR are performed on Australindolone A and C. 1D-NOESY is used to coordinate proton peaks to the 4-6 position of Australindolone A. Structural correlation of the novel compounds can lead to similar results in bioactivity. As previously stated, Meridianin A-E have been assayed with malaria, CNS, and several kinases projects. (Lebar, M. D., *Antarctic tunicates and endophytic fungi [electronic resource]: chemical investigation and synthesis*/by Matthew D. Lebar. [Tampa, Fla.]. University of South Florida, 2010; Gompel, M.; Leost, M.; De Kier Joffe, E. B.; Puricelli, L.; Franco, L. H.; Palermo, J.; Meijer, L., Meridianins, a new family of protein kinase inhibitors isolated from the Ascidian *Aplidium meridianum*. *Bioorganic & Medicinal Chemistry Letters* 2004, 14 (7), 1703-1707; Lebar, M. D.; Hahn, K. N.; Mutka, T.; Maignan, P.; McClintock, J. B.; Amsler, C. D.; van Olphen, A.; Kyle, D. E.; Baker, B. J., CNS and antimalarial activity of synthetic meridianin and psammopemmin analogs. *Bioorganic & medicinal chemistry* 2011, 19 (19), 5756-62; Walker, S. R.; Carter, E. J.; Huff, B. C.; Morris, J. C., Variolins and related alkaloids. *Chemical reviews* 2009, 109 (7), 3080-3098).

The results from these projects were promising. Therefore, the three newly found compounds, Australindolone A-C, are tested for these maladies using bioactivity assays. Meridianin A, specifically, has been submitted to Leishmaniasis assay and the result was also notable. Therefore, Meridianin B-H are submitted to the Leishmaniasis assay. Consequently, additional collections of these compounds are currently implemented, and that future endeavors of analyzing their structure-activity relationship (SAR) and possible synthesis pathways are also in the continuation of this research. Upon discovery, these new derivatives can further serve as precursors to other synthesizable structurally related analogues, and as an extension to the diversity of the Center for Excellence in Drug Discovery and Innovation (CDDI)'s standard library.

Australindolone D (4)

Figure 15:
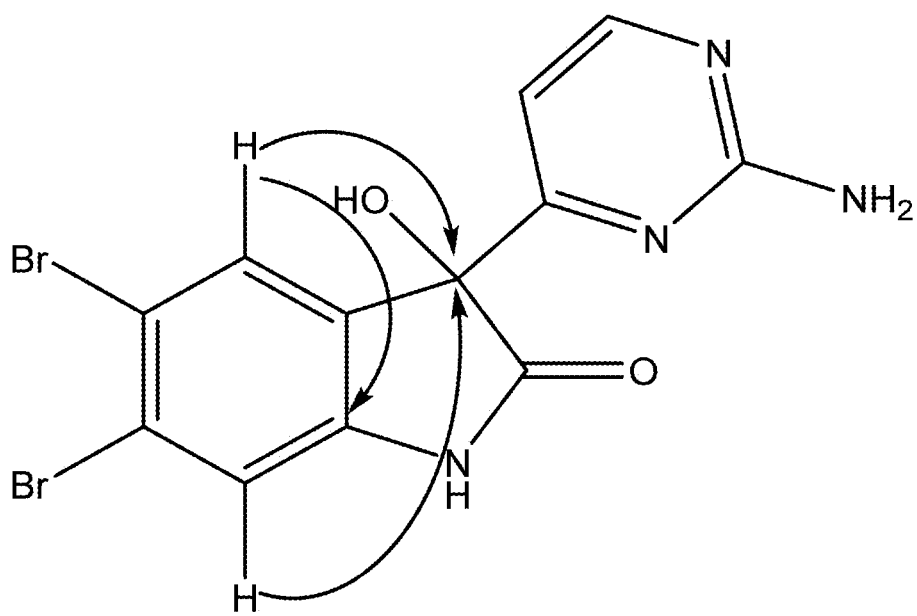
FIG. 15 is an image depicting Key COSY (bold) and HMBC (arrows) Correlations for Australindolone D.

Australindolone D (4) was the last compound isolated from the extract. It is a yellow solid and the molecular formula was determined as $C_{12}H_8N_4O_2Br_2$ ([M+H]$^+$: 398.9083, calculated 398.9092, $\Delta$=−0.9 amu), based on HRESIMS and the structure was elucidated using $^1$H and $^{13}$C NMR data. The 2-aminopyrimidine ring was resolved in a similar manner to the previous three compounds. The multiplicity of H-4 at 7.32 ppm (s) and H-7 at 7.21 ppm (s) suggested the positioning of the bromines being in positions 4 and 6, 5 and 6 or 5 and 7. The HMBC correlation of H-7 to C-3 indicated that the two Bromines could not be in positions 4 and 6. Using the upfield shift of C-5 and C-6, as well as the downfield shift of H-4, H-7 and the 3-OH the two Bromines were placed in positions 5 and 6. (FIG. 15)

TABLE 12

NMR spectroscopic data for australindolone D (4)$^a$

| | Australindolone D (4) | | |
|---|---|---|---|
| Position | $\delta_C{}^b$ | $\delta_H{}^c$ | HMBC |
| 1 NH | | 10.74 (1H, s) | |
| 2 | 177.2, C | | |
| 3 | 78.3, C | | |
| 3-OH | | 7.00 (1H, s) | |
| 3a | 135.2, C | | |
| 4 | 129.2, CH | 7.32 (1H, s) | 3, 3a, 5, 6, 7a |
| 5 | 115.8 C | | |
| 6 | 124.6 C | | |
| 7 | 115.1, CH | 7.21 (1H, s) | 3, 4, 5, 6, 7a |
| 7a | 144.0, C | | |
| 1' | — | — | — |
| 2' | 163.4, C | | |
| 2'-NH$_2$ | | 6.55 (2H, s) | 2', 4', 6' |
| 3' | — | — | — |
| 4' | 169.9, C | | |
| 5' | 106.3, CH | 7.00 (1H, d, 5) | 3, 4', 6' |
| 6' | 159.7, CH | 8.33 (1H, d, 5) | 3, 2', 4', 5' |

$^a$DMSO;
$^b$125 MHz, multiplicity (from HSQC);
$^c$400 MHz (integration, multiplicity, J (Hz))

Meridianin H (12)

Compound 12 was isolated as a yellow solid and the HRESIMS of it showed a molecular formula of $C_{12}H_8N_4O_2Br_2$ ([M+H]$^+$: m/z 382.9129, calculated 382.9143, $\Delta$=1.4 amu). The $^{13}$C NMR shifts indicated the presence of two heteroaromatic rings. The HMBC correlations of H-5' and H-6', combined with the carbon shifts of C-2', C-4' and C-6' indicated the presence of a pyrimidine ring, which was elucidated as a 2-aminopyrimidine. The $^{13}$C NMR and the $^1$H shift at 12.14 ppm, combined with the molecular formula of the remaining fragment ($C_8H_4Br_2NO$) strongly suggested the presence of an indole ring. The HMBC correlation of H-5' to C-3 guided the positioning of the 2-aminopyrimidine ring on C-3. The sharp deshielded signal at 15.04 ppm (s) indicated the presence of a hydroxyl group (exchangeable with $D_2O$). The C-3, C-3a and C-4 shifts indicated the position of the OH on C-4, further supported by the HMBC correlations to C-4 and C-6. Similarly, the HMBC correlations between H-2, indicated the position of C-3a and C-7a. The position of the two bromines was guided by the HMBC correlations of H-6 and the upfield shifts of C-5 and C-7 and was further supported by the multiplicity of H-6 (s). Additional NMR data is shown in Table 13 below:

TABLE 13

NMR spectroscopic data for meridianin H (12)[a]

| Position | $\delta_C$[b] | $\delta_H$[c] | HMBC |
|---|---|---|---|
| 1 NH | | 12.14 (1H, s) | |
| 2 | 130.0, CH | 8.34 (1H, s) | 3, 3a, 7a |
| 3 | 114.7, C | | |
| 3a | 116.3, C | | |
| 4 | 148.7, C | | |
| 4-OH | | 15.07 (1H, s) | 4, 6 |
| 5 | 99.1, C | | |
| 6 | 128.6, CH | 7.42 (1H, s) | 4, 5, 7, 7a |
| 7 | 93.0, C | | |
| 7a | 136.1, C | | |
| 1' | — | — | — |
| 2' | 161.4, C | | |
| 2'-NH$_2$ | | 6.91 (2H, s) | |
| 3' | — | — | |
| 4' | 159.3, C | | |
| 5' | 104.6, CH | 7.23 (1H, d, 5) | 3, 4', 6' |
| 6' | 159.4, CH | 8.17 (1H, d, 5) | 4', 5' |

[a]DMSO;
[b]125 MHz, multiplicity (from HSQC);
[c]400 MHZ (integration, multiplicity, J (Hz).

Once the structures of the novel Meridianin and Australindolones were elucidated, a number of synthetic methods may be used to synthetically construct the Meridianin and Australindolones for use in the pharmaceutical compositions described herein. Such synthetic methods include, but are not limited to, those contained in Walker, S. R.; J. C. Chem. Rev. 2009, 109, 3080, herein incorporated by reference into this disclosure. For example, the Meridianin and Australindolones can be synthesized via disconnection of the indole as an intact unit and either construction of the pyrimidine ring onto an 5-acylated indole or connection of an intact pyrimidine ring to an indole system via a Suzuki coupling reaction. However, other methods including, but not limited to, other methods listed in Walker 2009 are contemplated and included in this disclosure.

Example 4—Phenotypic Zebrafish Bioassay

Marine natural products have increasingly attracted the interest of the scientific community over the past several decades. This is largely attributable to a growing appreciation of the geographic dominance of the world's oceans (covering 70% of the earth), and with the general consensus that life first evolved in the sea. The vast chemodiversity attributed to marine invertebrates is most likely the result of their extensive evolutionary history and their colonization of a wide array of different marine environments where selective pressures are certain to vary considerably. The Southern Ocean surrounding Antarctica is vast and remote, and despite its fauna having a rich biodiversity and high endemicity, the continent and its surrounding seas have received little attention in terms of marine natural products chemistry. Here, an Antarctic tunicate was the source of twelve indole alkaloids. Tunicates depend on their chemical defense to protect them from predators and as such have proven to be a good source for novel compounds. The inventors investigated the chemistry of the tunicate Synoicum sp., known commonly as the 'yellow top' tunicate. The inventors discovered novel meridianin alkaloids and their indolone derivatives. The meridianin indole alkaloids were originally isolated from the tunicate Aplidium meridianum obtained in the South Atlantic Ocean. As noted above, the inventors discovered five new compounds (Australindolones A-D and Meridianin H). The inventors conducted experiments in a series of phenotypic zebrafish assays to determine the activity of the known compounds as well as the new compounds.

Bioassay Procedure

Wildtype Danio rerio fish were used for the assay. Once the zebrafish eggs were collected, they were placed in fresh media along with methylene blue, to deter fungal growth. The embryos were sorted and placed in a 96-well plate and the volume was standardized. For the purpose of this screening it was determined that the optimal point to add the compounds was 4 hours post fertilization and the ending point of the assay was 24 hours post fertilization. The delay in growth and the dysmorphologies were monitored and assessed.

Bioassay Data

A developmental zebrafish assay was utilized to test the activity of the extract, the subsequent fractions, and the isolated compounds. As part of a screening project, the extract of Synoicum sp. was one of the leading hits in the assay. The zebrafish embryos displayed dysmorphologies and an interesting phenotype at various different concentrations and time points as can be seen in Table 14 below. The Maximum Tolerated Concentration (MTC) was determined for each compound, alongside the minimum active concentration for each compound. The final tested concentration was determined as the one most representative of the phenotype.

TABLE 14

MTC and final tested concentration
for Meridianins A-H and Australindolones A-D

| | MTC | Final C tested |
|---|---|---|
| Meridianin A | 100 uM | 30 uM |
| Meridianin B | 300 uM | 100 uM |
| Meridianin C | 10 uM | 3 uM |
| Meridianin D | 100 uM | 65 uM |
| Meridianin E | 100 uM | 10 uM |
| Meridianin F | 10 uM | 2 uM |
| Meridianin G | 300 uM | 100 uM |
| Meridianin H | 100 uM | 60 uM |
| Australindolone A | 1 mM | 300 uM |
| Australindolone B | 1 mM | 300 uM |
| Australindolone C | 1 mM | 300 uM |
| Australindolone D | 1 mM | 300 uM |

Figure 16:
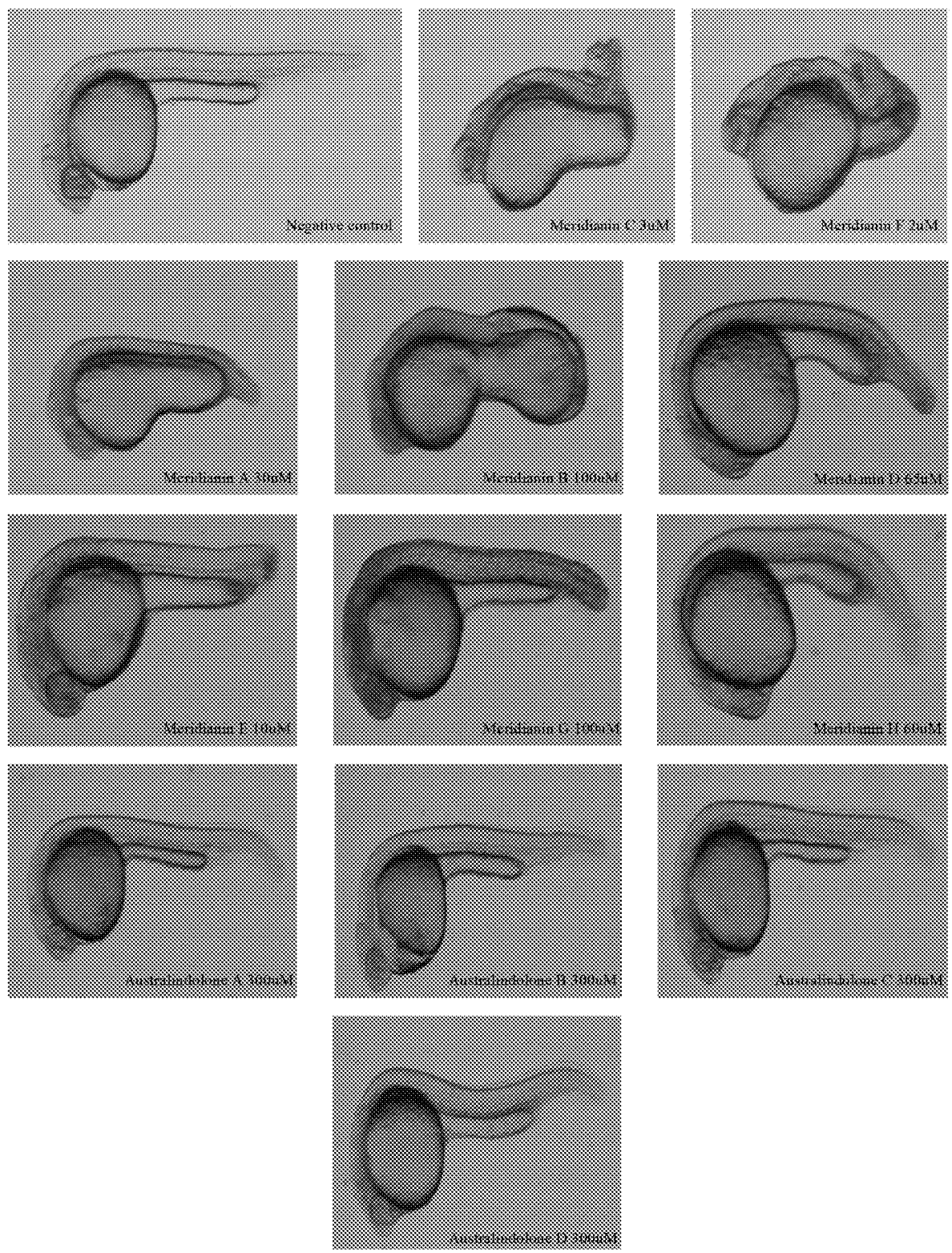
FIG. 16 is a series of images depicting Zebrafish embryonic development for bioactivity determination (24h post-fertilization) for Meridianins A-H and Australindolones A-D. Representative embryos treated with meridianin C (top middle) and meridianin F (top right) revealed truncation of the anterior-posterior axis as compared to control (top left).

The focus was placed on Meridianins C and F, which demonstrated two interesting phenotypes at low concentrations (3 uM and 2 uM respectively). These Meridianins exhibited toxicity at concentrations above 10 μM. The images shown in FIG. 16 illustrate each phenotype for the 12 compounds alongside the control.

Although 12 different phenotypes were observed from the pure compounds, none was a match for the original one of the screening, which was attributed to synergistic effects between the compounds in the crude extract.

Several signaling pathways were identified as potential targets based on the truncation of the anterior-posterior axis that can be observed. As a result of this particular phenotypic observation, a kinase screening was deemed necessary and 3 potential pathways were identified. A comparison of the human and zebrafish kinome was performed through literature search to identify the common kinases on the possible pathways of the two species. As a result, the compounds are further subjected to a kinase screening to identify their potential targets.

The three identified pathways were BMP (bone morphogenic protein), JAK (Janus kinase) and MAP (mitogen-activated protein kinase). After comparison of the two kinomes, 33 kinases were selected that could be found in both species and had a similarity between 60-96%. According to the literature, there is a high degree of identity between the catalytic domains of kinases of the two species, but there are multiple zebrafish kinases with no close human counterpart. (Mucha, B. E.; Hashiguchi, M.; Zinski, J.; Shore, E. M.; Mullins, M. C. Variant BMP Receptor Mutations Causing Fibrodysplasia Ossificans Progressiva (FOP) in Humans Show BMP Ligand-Independent Receptor Activation in Zebrafish. *Bone* 2018, 109, 225-231; Martinez-Navarro, F. J.; Martinez-Menchón, T.; Mulero, V.; Galindo-Villegas, J. Models of Human Psoriasis: Zebrafish the Newly Appointed Player. *Developmental & Comparative Immunology* 2019, 97, 76-87; Shin, Y. S.; Hwang, H. S.; Kang, S. U.; Chang, J. W.; Oh, Y.-T.; Kim, C.-H. Inhibition of P38 Mitogen-Activated Protein Kinase Ameliorates Radiation-Induced Ototoxicity in Zebrafish and Cochlea-Derived Cell Lines. *NeuroToxicology* 2014, 40, 111-122; Hogan, B. M.; Schulte-Merker, S. How to Plumb a Pisces: Understanding Vascular Development and Disease Using Zebrafish Embryos. *Developmental Cell* 2017, 42 (6), 567-583; Wlodarchak, N.; Tariq, R.; Striker, R. Comparative Analysis of the Human and Zebrafish Kinomes: Focus on the Development of Kinase Inhibitors. 2016, 21; Sanvitale, C. E.; Kerr, G.; Chaikuad, A.; Ramel, M.-C.; Mohedas, A. H.; Reichert, S.; Wang, Y.; Triffitt, J. T.; Cuny, G. D.; Yu, P. B.; Hill, C. S.; Bullock, A. N. A New Class of Small Molecule Inhibitor of BMP Signaling. *PLoS ONE* 2013, 8 (4), e62721).

Example 5—Prophetic Method of Treating Kinase Disorder (Alzheimer's Disease)

A 70 year old female patient presents with memory loss, personality changes, problems using language, disorientation and difficulty performing daily activities. The patient diagnoses with Alzheimer's disease. The patient is orally administered a therapeutically effective amount of a pharmaceutical composition containing synthetic Meridianin H and a pharmaceutically acceptable carrier. Improvement is seen in the symptoms after treatment over a given time period with decreased disorientation and improvement in language and memory.

A 65 year old male patient presents with disorientation and memory loss. The patient diagnoses with Alzheimer's disease. The patient is orally administered a therapeutically effective amount of a pharmaceutical composition containing synthetic Australindolone A and a pharmaceutically acceptable carrier. Improvement is seen in the symptoms after treatment over a given time period with decreased disorientation and improvement in memory.

A 72 year old male patient presents with confusion, memory loss and difficulty in understanding spatial relationships. The patient diagnoses with Alzheimer's disease. The patient is orally administered a therapeutically effective amount of a pharmaceutical composition containing synthetic Australindolone B and a pharmaceutically acceptable carrier. Improvement is seen in the symptoms after treatment over a given time period with decreased confusion and improvement in memory and spatial relationship understanding.

A 78 year old female patient presents with confusion, disorientation, and memory loss. The patient diagnoses with Alzheimer's disease. The patient is orally administered a therapeutically effective amount of a pharmaceutical composition containing synthetic Australindolone C and a pharmaceutically acceptable carrier. Improvement is seen in the symptoms after treatment over a given time period with decreased confusion and disorientation and improvement in memory.

A 68 year old male patient presents with confusion, personality changes and memory loss. The patient diagnoses with Alzheimer's disease. The patient is orally administered a therapeutically effective amount of a pharmaceutical composition containing synthetic Australindolone D and a pharmaceutically acceptable carrier. Improvement is seen in the symptoms after treatment over a given time period with decreased confusion and improvement in memory.

Example 6—Prophetic Method of Treating Malaria

A 30 year old male patient presents with chills, headache, muscle aches, fatigue, nausea, and vomiting. The patient diagnoses with malaria. The patient is orally administered a therapeutically effective amount of a pharmaceutical composition containing synthetic Meridianin H and a pharmaceutically acceptable carrier. After repeated administrations over a given time period, improvement is seen in the symptoms.

A 40 year old female patient presents with fever, chills, headache, muscle aches, fatigue, nausea, and vomiting. The patient diagnoses with malaria. The patient is orally administered a therapeutically effective amount of a pharmaceutical composition containing synthetic Australindolone A and a pharmaceutically acceptable carrier. After repeated administrations over a given time period, improvement is seen in the symptoms.

A 28 year old female patient presents with fever, chills, muscle aches, fatigue, nausea, and vomiting. The patient diagnoses with malaria. The patient is orally administered a therapeutically effective amount of a pharmaceutical composition containing synthetic Australindolone B and a pharmaceutically acceptable carrier. After repeated administrations over a given time period, improvement is seen in the symptoms.

A 48 year old female patient presents with fever, chills, headache, fatigue, and nausea. The patient diagnoses with malaria. The patient is orally administered a therapeutically effective amount of a pharmaceutical composition containing synthetic Australindolone C and a pharmaceutically acceptable carrier. After repeated administrations over a given time period, improvement is seen in the symptoms.

A 35 year old male patient presents with fever, chills, muscle aches, fatigue, nausea, and vomiting. The patient diagnoses with malaria. The patient is orally administered a therapeutically effective amount of a pharmaceutical composition containing synthetic Australindolone D and a pharmaceutically acceptable carrier. After repeated administrations over a given time period, improvement is seen in the symptoms.

Example 7—Prophetic Method of Treating Lung Adenocarcinoma

A 58 year old male patient presents with chronic cough, coughing up blood and shortness of breath. The patient diagnoses with non-small cell lung cancer, specifically adenocarcinoma of the lung. After surgery, the patient is parenterally administered a therapeutically effective amount of a pharmaceutical composition containing synthetic Meridianin H and a pharmaceutically acceptable carrier. After repeated administrations over a given time period, improvement is seen in the symptoms.

A 65 year old female patient presents with chronic cough, coughing up blood, chest pain and shortness of breath. The patient diagnoses with non-small cell lung cancer, specifically adenocarcinoma of the lung. After surgery, the patient is parenterally administered a therapeutically effective amount of a pharmaceutical composition containing synthetic Australindolone A and a pharmaceutically acceptable carrier. After repeated administrations over a given time period, improvement is seen in the symptoms.

A 70 year old male patient presents with chronic cough, coughing up blood, chest pain, unexplained weight loss and shortness of breath. The patient diagnoses with non-small cell lung cancer, specifically adenocarcinoma of the lung. After surgery, the patient is parenterally administered a therapeutically effective amount of a pharmaceutical composition containing synthetic Australindolone B and a pharmaceutically acceptable carrier. After repeated administrations over a given time period, improvement is seen in the symptoms.

A 62 year old female patient presents with chronic cough, coughing up blood, unexplained weight loss and shortness of breath. The patient diagnoses with non-small cell lung cancer, specifically adenocarcinoma of the lung. After surgery, the patient is parenterally administered a therapeutically effective amount of a pharmaceutical composition containing synthetic Australindolone C and a pharmaceutically acceptable carrier. After repeated administrations over a given time period, improvement is seen in the symptoms.

A 68 year old male patient presents with chronic cough, coughing up blood, chest pain, unexplained weight loss and shortness of breath. The patient diagnoses with non-small cell lung cancer, specifically adenocarcinoma of the lung. After surgery, the patient is parenterally administered a therapeutically effective amount of a pharmaceutical composition containing synthetic Australindolone D and a pharmaceutically acceptable carrier. After repeated administrations over a given time period, improvement is seen in the symptoms.

CONCLUSION

The inventors have identified five new Meridianin and Australindolone compounds isolated from the Antarctic tunicate *Synoicum* sp., known commonly as the 'yellow top' tunicate. The inventors have isolated the compounds to determine their structure. Now that the structure is known, the compounds can be synthetically manufactured for various uses as pharmaceutical compositions. Exemplary uses of the pharmaceutical compositions include, but are not limited to, treatment of kinase disorders and parasitic infections.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

The disclosures of all publications cited above are expressly incorporated herein by reference, each in its entirety, to the same extent as if each were incorporated by reference individually.

While there has been described and illustrated specific embodiments of the meridianin compositions and methods of treating diseases, including but not limited to, parasitic infections and kinase diseases, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

It is also to be understood that the following claims are intended to cover all of the generic and specific features of the invention herein described, and all statements of the scope of the invention which, as a matter of language, might be said to fall there between. Now that the invention has been described,

What is claimed is:

1. A pharmaceutical composition consisting of:
a synthetic compound of formula I:

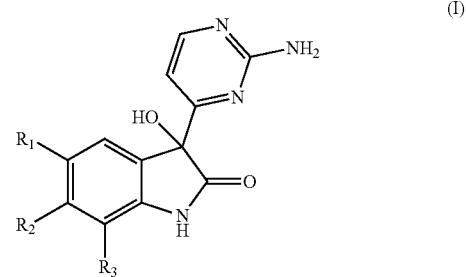

(I)

wherein $R^1$ is hydrogen or bromine;
wherein $R^2$ is hydrogen or bromine; and
wherein $R^3$ is hydrogen; and
a pharmaceutically acceptable carrier;
wherein the pharmaceutical composition is in a form of an emulsion.

2. The composition of claim 1, wherein both $R^1$ and $R^2$ are hydrogen.

3. The composition of claim 1, wherein $R^1$ is hydrogen and $R^2$ is bromine.

4. The composition of claim 1, wherein $R^1$ is bromine and $R^2$ is hydrogen.

5. The composition of claim 1, wherein both $R^1$ and $R^2$ are bromine.

* * * * *